US011680297B2

(12) United States Patent
Xing et al.

(10) Patent No.: US 11,680,297 B2
(45) Date of Patent: Jun. 20, 2023

(54) ACTIVITIES OF MULTIPLE CANCER-RELATED PATHWAYS ARE ASSOCIATED WITH BRAF MUTATION AND PREDICT THE RESISTANCE TO BRAF/MEK INHIBITORS IN MELANOMA CELLS

(71) Applicant: THE JOHNS HOPKINS UNIVERSITY, Baltimore, MD (US)

(72) Inventors: Michael Mingzhao Xing, Clarksville, MD (US); Dingxie Liu, Hancock, MI (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 273 days.

(21) Appl. No.: 15/022,022

(22) PCT Filed: Sep. 16, 2014

(86) PCT No.: PCT/US2014/055884
§ 371 (c)(1),
(2) Date: Mar. 15, 2016

(87) PCT Pub. No.: WO2015/039107
PCT Pub. Date: Mar. 19, 2015

(65) Prior Publication Data
US 2016/0222466 A1 Aug. 4, 2016

Related U.S. Application Data

(60) Provisional application No. 61/878,338, filed on Sep. 16, 2013.

(51) Int. Cl.
*C12Q 1/6886* (2018.01)
*G01N 33/574* (2006.01)
*G01N 33/50* (2006.01)

(52) U.S. Cl.
CPC ....... *C12Q 1/6886* (2013.01); *G01N 33/5011* (2013.01); *G01N 33/5743* (2013.01); *C12Q 2600/106* (2013.01); *C12Q 2600/158* (2013.01); *G01N 2333/525* (2013.01); *G01N 2333/56* (2013.01); *G01N 2333/57* (2013.01); *G01N 2333/71* (2013.01); *G01N 2800/52* (2013.01)

(58) Field of Classification Search
None
See application file for complete search history.

(56) References Cited

U.S. PATENT DOCUMENTS

| 8,426,418 B2 | 4/2013 | Coopersmith et al. |
| 9,279,144 B2 | 3/2016 | Garraway et al. |
| 9,481,910 B2 | 11/2016 | Rosen et al. |
| 2011/0091377 A1 | 4/2011 | Alani et al. |
| 2012/0053185 A1 | 3/2012 | Coopersmith et al. |
| 2013/0004509 A1 | 1/2013 | Garraway |
| 2013/0217721 A1 | 8/2013 | Lo et al. |

FOREIGN PATENT DOCUMENTS

WO 2017099591 A1 6/2017

OTHER PUBLICATIONS

Pirooznia et al. BMC Genomics 9(Suppl 1):S13 Mar. 20, 2008.*
Augustine et al. (2010) (copy of citation #10 in specification).*
Brychtova, S., et al., "Stromal microenvironment alterations in malignant melanoma" Research on Melanoma—A Glimpse into Current Directions and Future Trends (2011) Chapter 16, pp. 335-260.
Smalley, K., "Understanding melanoma signaling networks as the basis for molecular targeted therapy", (2010) Journal of Investigative Dermatology, vol. 130, No. 1, pp. 28-37.
Bollag et al., "Vemurafenib: the first drug approved for BRAF-mutant cancer.", Nat Rev Drug Discov 2012;11:873-86.
Sullivan et al., "MAP kinase signaling and inhibition in melanoma." Oncogene 2013;32:2373-9.
Chapman et al., "Improved survival with vemurafenib in melanoma with BRAF V600E mutation." N Engl J Med 2011;364:2507-16.
Fedorenko et al., "Acquired and intrinsic BRAF inhibitor resistance in BRAF V600E mutant melanoma." Biochem Pharmacol 2011;82:201-9.
Subramanian et al., "Gene set enrichment analysis: a knowledge-based approach for interpreting genome-wide expression profiles." Proc Natl Acad Sci U S A 2005;102:15545-50.
Bild et al., "Oncogenic pathway signatures in human cancers as a guide to targeted therapies." Nature 2006;%19;439:353-7.
Gatza et al., "A pathway-based classification of human breast cancer." Proc Natl Acad Sci U S A 2010;107:6994-9.
Freedman et al., "Use of gene expression and pathway signatures to characterize the complexity of human melanoma." Am J Pathol 2011;178:2513-22.
Gatza et al., "Analysis of tumor environmental response and oncogenic pathway activation identifies distinct basal and luminal features in HER2-related breast tumor subtypes." Breast Cancer Res 2011;13:R62.

(Continued)

*Primary Examiner* — Joseph Woitach
(74) *Attorney, Agent, or Firm* — Johns Hopkins Technology Ventures

(57) ABSTRACT

The present inventors have identified specific oncogenic pathways preferentially activated in BRAF-mutated-melanoma cells and a pathway pattern that predicts resistance of BRAF-mutated melanoma to BRAF/MEK inhibitors, providing novel clinical implications for melanoma therapy. In one embodiment, a method comprises (a) testing a sample oiBRAF-mutated melanoma cells isolated from a patient and measuring the expression levels of genes expressed in the following oncogenic pathways: TNFa, EGFR, IFNa, hypoxia, IFNy, STAT3 and Myc; (b) calculating a 7-pathway activation pattern based on the measured expression levels of step (a); and (c) identifying the patient's resistance level to BRAF/MEK inhibitor treatment based on comparison of the calculated 7-pathway activation pattern to a reference.

2 Claims, 17 Drawing Sheets

Specification includes a Sequence Listing.

(56) References Cited

OTHER PUBLICATIONS

West et al., "Embracing the complexity of genomic data for personalized medicine." Genome Res 2006;16:559-66.
Johansson et al., "Confirmation of a BRAF mutation-associated gene expression signature in melanoma." Pigment Cell Res 2007;20:216-21.
Zhuang et al., "C-MYC overexpression is required for continuous suppression of oncogene-induced senescence in melanoma cells." Oncogene 2008;27:6623-34.
Putzer et al., "Predicting and preventing melanoma invasiveness: advances in clarifying E2F1 function." Expert Rev Anticancer Ther 2010;10:1707-20.
Damsky et al., "beta-catenin signaling controls metastasis in Braf-activated Pten-deficient melanomas." Cancer Cell 2011;20:741-54.
Satyamoorthy et al., "Insulin-like growth factor-1 induces survival and growth of biologically early melanoma cells through both the mitogen-activated protein kinase and beta-catenin pathways" Cancer Res 2001;61:7318-24.
Li et al., "Are interactions with p63 and p73 involved in mutant p53 gain of oncogenic function?" Oncogene 2007;26:2220-5.
Davies et al., "Analysis of the genome to personalize therapy for melanoma." Oncogene 2010;29:5545-55.
Croce, "Oncogenes and cancer." N Engl J Med 2008;358:502-11.
Johnson et al., Adjusting batch effects in microarray expression data using empirical Bayes methods., Biostatistics 2007;8:118-27.
Liu et al., Epigenetic genes regulated by the BRAFV600E signaling are associated with alterations in the methylation and expression of tumor suppressor genes and patient survival in melanoma. Biochem Biophys Res Commun 2012;425:45-50.
Ellerhorst et al., Clinical correlates of NRAS and BRAF mutations in primary human melanoma. Clin Cancer Res 2011;17:229-35.
Dankort et al., Braf(V600E) cooperates with Pten loss to induce metastatic melanoma. Nat Genet 2009;41:544-52.
Hoek., DNA microarray analyses of melanoma gene expression: a decade in the mines. Pigment Cell Res 2007;20:466-84.
Kupas et al., RANK is expressed in metastatic melanoma and highly upregulated on melanoma-initiating cells. J Invest Dermatol 2011;131:944-55.
Girotti et al., Inhibiting EGF receptor or SRC family kinase signaling overcomes BRAF inhibitor resistance in melanoma. Cancer Discov 2013;3:158-67.
Held et al., Genotype-selective combination therapies for melanoma identified by high-throughput drug screening. Cancer Discov 2013;3:52-67.
Bertazza et al., The dual role of tumor necrosis factor (TNF) in cancer biology. Curr Med Chem 2010;17:3337-52.
Khodarev et al., Molecular pathways: interferon/stat1 pathway: role in the tumor resistance to genotoxic stress and aggressive growth. Clin Cancer Res 2012;18:3015-21.
Wang et al., Tumor necrosis factor alpha-dependent drug resistance to purine and pyrimidine analogues in human colon tumor cells mediated through IKK. J Biol Chem 2005;280:7634-44.
Yasuoka et al., Combination of tumor necrosis factor alpha and interferon alpha induces apoptotic cell death through a c-myc-dependent pathway in p53 mutant H226br non-small-cell lung cancer cell line. Exp Cell Res 2001;271:214-22.
Klefstrom et al., Induction of TNF-sensitive cellular phenotype by c-Myc involves p53 and impaired NF-kappaB activation. EMBO J 1997;16:7382-92.
Boccellino et al., Apoptosis induced by interferon-alpha and antagonized by EGF is regulated by caspase-3-mediated cleavage of gelsolin in human epidermoid cancer cells. J Cell Physiol 2004;201:71-83.
Yamaoka et al., Transactivation of EGF receptor and ErbB2 protects intestinal epithelial cells from TNF-induced apoptosis. Proc Natl Acad Sci U S A 2008;%19;105:11772-7.
Caraglia et al., alpha-Interferon potentiates epidermal growth factor receptor-mediated effects on human epidermoid carcinoma KB cells. Int J Cancer 1995;61:342-7.
Carlberg et al., Tumor necrosis factor and gamma-interferon repress transcription from the c-myc P2 promoter by reducing E2F binding activity. Int J Oncol 1999;15:121-6.
Harvey et al., Interferon-alpha-2b downregulation of oncogenes H-ras, c-raf-2, c-kit, c-myc, c-myb and c-fos in ESKOL, a hairy cell leukemic line, results in temporal perturbation of signal transduction cascade. Leuk Res 1994;18:577-85.
Li et al., Mechanisms of c-myc degradation by nickel compounds and hypoxia. PLoS One 2009;4:e8531.
Gerber et al., IFN-alpha induces transcription of hypoxia-inducible factor-1alpha to inhibit proliferation of human endothelial cells. J Immunol 2008;181:1052-62.
Hellwig-Burgel et al., Review: hypoxia-inducible factor-1 (HIF-1): a novel transcription factor in immune reactions. J Interferon Cytokine Res 2005;25:297-310.
Johnston et al., STAT3 signaling: anticancer strategies and challenges. Mol Interv 2011;11:18-26.
Grivennikov et al., Dangerous liaisons: STAT3 and NF-kappaB collaboration and crosstalk in cancer. Cytokine Growth Factor Rev 2010;21:11-9.
Mamlouk et al., Hypoxia-inducible factors as key regulators of tumor inflammation. Int J Cancer 2013;132:2721-9.
Majewski et al., Taming the dragon: genomic biomarkers to individualize the treatment of cancer. Nat Med 2011;17:304-12.
Straussman et al. Tumour micro-environment elicits innate resistance to RAF inhibitors through HGF secretion. Nature (2012), 486:500-4.
Lens et al., "Global Perspectives of contemporary epidemiological trends of cutaneous malignant melanoma." Br J Dermatol 2004; 150:179-85.
Joseph et al., The RAF inhibitor PLX4032 inhibits ERK signaling and tumor cell proliferation in a V600E BRAF-selective manner. Proc Natl Acad Sci U S A 2010;107:14903-8.
Pratilas et al., (V600E)BRAF is associated with disabled feedback inhibition of RAF-MEK signaling and elevated transcriptional output of the pathway. Proc Natl Acad Sci U S A 2009;106:4519-24.
Hoeflich et al., Antitumor efficacy of the novel RAF inhibitor GDC-0879 is predicted by BRAFV600E mutational status and sustained extracellular signal-regulated kinase/mitogen-activated protein kinase pathway suppression. Cancer Res 2009;69:3042-51.
Schweppe et al., Deoxyribonucleic acid profiling analysis of 40 human thyroid cancer cell lines reveals cross-contamination resulting in cell line redundancy and misidentification. J Clin Endocrinol Metab 2008;93:4331-41.
Wang et al., Hypoxia promotes ligand-independent EGF receptor signaling via hypoxia-inducible factor-mediated upregulation of caveolin-1. Proc Natl Acad Sci U S A 2012; 109:4892-7.
Casa et al., Estrogen and insulin-like growth factor-I (IGF-I) independently down-regulate critical repressors of breast cancer growth. Breast Cancer Res Treat 2012;132:61-73.
Piva et al. Functional validation of the anaplastic lymphoma kinase signature identifies CEBPB and BCL2A1 as critical target genes. J Clin Invest 2006;116:3171-82.
Sakamoto et al., CH5424802, a selective ALK inhibitor capable of blocking the resistant gatekeeper mutant. Cancer Cell 2011;19:679-90.
Augustine et al., Gene expression signatures as a guide to treatment strategies for in-transit metastatic melanoma. Mol Cancer Ther 2010;9:779-90.
Augustine et al., Genomic and molecular profiling predicts response to temozolomide in melanoma. Clin Cancer Res 2009;15:502-10.
Raskin et al. Transcriptome Profiling Identifies HMGA2 as a Biomarker of Melanoma Progression and Prognosis. J Invest Dermatol 2013;10.
Bloethner et al., Effect of common B-RAF and N-RAS mutations on global gene expression in melanoma cell lines. Carcinogenesis 2005;26:1224-32.
Widmer et al., Systematic classification of melanoma cells by phenotype-specific gene expression mapping. Pigment Cell Melanoma Res 2012;25:343-53.
Van Malenstein et al., A seven-gene set associated with chronic hypoxia of prognostic importance in hepatocellular carcinoma. Clin Cancer Res 2010;16:4278-88.

(56) References Cited

OTHER PUBLICATIONS

Hoek et al., Metastatic potential of melanomas defined by specific gene expression profiles with no BRAF signature. Pigment Cell Res 2006;19:290-302.

Chang et al., LIBSVM : a library for support vector machines. ACM Transactions on Intelligent Systems and Technology 2011;2:1-27.

Liu et al., Genetic alterations in the phosphoinositide 3-kinase/Akt signaling pathway confer sensitivity of thyroid cancer cells to therapeutic targeting of Akt and mammalian target of rapamycin. Cancer Res 2009;69:7311-9.

Guyon et al. Gene Selection for Cancer Classification using Support Vector Machines. Machine Learning 2002;46:389-422.

Dry et al., Transcriptional pathway signatures predict MEK addiction and response to selumetinib (AZD6244). Cancer Res 2010;70:2264-73.

Terui et al., Hypoxia/re-oxygenation-induced, redox-dependent activation of STAT1 (signal transducer and activator of transcription 1) confers resistance to apoptotic cell death via hsp70 induction. Biochem J 2004;380:203-9.

Yu et al., Mechanism of TNF-alpha autocrine effects in hypoxic cardiomyocytes: initiated by hypoxia inducible factor I-alpha, presented by exosomes. J Mol Cell Cardiol 2012; 53:848-57.

Wilson et al., Widespread potential for growth-factor-driven resistance to anticancer kinase inhibitors. Nature 2012;487:505-9.

Nazarian et al., Melanomas acquire resistance to B-RAF(V600E) inhibition by RTK or N-RAS upregulation., Nature (2010); 468:973-977.

Villaneuva et al., REsistance to BRAF inhibitors: unraveling mechanisms and future treatment options. Cancer Res. 2011, 71(23): 7137-40.

Welsh et al., Resistance to combination BRAF and MEK inhibition in metastatic melanoma: Where to next?, European Journal of Cancer 2016;62:76-85.

\* cited by examiner

TO FIG. 10B

ACTIVITIES OF MULTIPLE CANCER-RELATED PATHWAYS ARE ASSOCIATED WITH BRAF MUTATION AND PREDICT THE RESISTANCE TO BRAF/MEK INHIBITORS IN MELANOMA CELLS

CROSS-REFERENCE TO RELATED APPLICATIONS

This application is a 35 U.S.C. § 371 U.S. national entry of International Application PCT/US2014/055884 having an international filing date of Sep. 16, 2014, which claims the benefit of U.S. Provisional Application No. 61/878,338, filed Sep. 16, 2013, the content of each of the aforementioned applications is herein incorporated by reference in their entirety.

STATEMENT OF GOVERNMENTAL INTEREST

This invention was made with government support under grant no. R01 CA134225, awarded by the National Institutes of Health. The government has certain rights in the invention.

FIELD OF THE INVENTION

The present invention relates to the field of cancer. More specifically, the present invention provides methods and compositions useful in the assessment and treatment of cancer.

INCORPORATION-BY-REFERENCE OF MATERIAL SUBMITTED ELECTRONICALLY

This application contains a sequence listing. It has been submitted electronically via EFS-Web as an ASCII text file entitled "P12704-02_ST25.txt." The sequence listing is 4,210 bytes in size, and was created on Sep. 16, 2014. It is hereby incorporated by reference in its entirety.

BACKGROUND OF THE INVENTION

Melanoma is a highly aggressive skin cancer that originates from melanocytes and its incidence has been rising substantially over the past decades worldwide (1). A prominent molecular pathological characteristic of melanoma is that gene mutations in the BRAF/MEK pathway are highly prevalent (2, 3). Among them is the BRAF T1799A, which results in BRAFV600E that possesses constitutively activated BRAF kinase activities. This is the most common mutation in melanoma, occurring in about 50% of cases (2, 3).

Several BRAF/MEK signaling pathway inhibitors, including inhibitors selectively against BRAFV600E or its downstream molecular MEK, have shown prominent effects in melanoma patients in recent clinical trials (2, 4). One of the major clinical obstacles in this molecular-targeted therapy is, however, the commonly seen innate drug resistance. As an example, about 20% to 40% of patients with BRAF-mutated melanoma do not respond to the BRAFV600E inhibitor PLX4032 (2-5). Thus, novel treatment strategies and biomarkers for prediction of such drug resistance are urgently needed to improve the response rates and the duration of clinical benefit. In this context, it is interesting that several molecular abnormalities, such as the activation of hepatocyte growth factor (HGF)/MET signaling, amplification of cyclin D1 (CCND1), CDK4-activating mutations, and loss of phosphatase and tensin homolog (PTEN) or retinoblastoma protein (RB1), have been recently found to be associated with the innate resistance to BRAF/MEK signaling inhibitors in a small range of BRAF-mutated cancer cells [reviewed in Ref (2, 3, 5)]. Identification of more universal biomarkers for predicting drug resistance is in need to facilitate the development of novel strategies tacking the drug resistance issues in melanoma.

Several approaches, such as gene set enrichment analysis (GSEA) and Bayesian binary regression (BinReg), have been developed to generate cell signaling pathway profiling based on gene expression data (6, 7). The advantage of BinReg approach is that it can provide a quantitative measure of pathway activation for individual samples. Pathway profiling based on this approach has been successfully used to differentiate tumor subtypes, identify molecular pathologies of diseases, and predict clinical outcomes and drug response of cancer patients (7-11). In the present study, we used BinReg approach to analyze the activities of 24 cancer-related pathways in melanoma cells and identified a pathway pattern that was able to predict the resistance of BRAF-mutated melanoma cells to BRAF/MEK signaling inhibitors. Moreover, we also examined and identified patterns of the activation of multiple oncogenic pathways that occurred preferentially in BRAF-mutated melanoma cells, especially in cells carrying both BRAF and PTEN abnormalities, which uniquely linked the molecular pathologies and clinical features of melanoma.

SUMMARY OF THE INVENTION

Drug resistance is a major obstacle in the targeted therapy of melanoma using BRAF/MEK inhibitors. This study was to identify BRAF V600E-associated oncogenic pathways that predict resistance of BRAF-mutated melanoma to BRAF/MEK inhibitors.

We took in silico approaches to analyze the activities of 24 cancer-related pathways in melanoma cells and identify those whose activation was associated with BRAF V600E and used the support vector machine (SVM) algorithm to predict the resistance of BRAF-mutated melanoma cells to BRAF/MEK inhibitors based on pathway activation patterns. We then experimentally confirmed the in silico findings.

In a microarray gene expression dataset of 63 melanoma cell lines, activation of multiple oncogenic pathways preferentially occurred in BRAF-mutated melanoma cells. This finding was reproduced in 5 additional independent melanoma datasets. Analysis of 46 melanoma cell lines that harbored BRAF mutation showed that 7 pathways, including TNFα, EGFR, IFNα, hypoxia, IFNγ, STAT3 and MYC, were particularly upregulated in AZD6244-resistant compared with responsive melanoma cells. A SVM classifier built on this 7-pathway activation pattern correctly predicted the response of 10 BRAF-mutated melanoma cell lines to the MEK inhibitor AZD6244 in our experiments. We also experimentally showed that TNFα, EGFR, IFNα, and IFNγ pathway activities were upregulated in melanoma cell A375 compared with its sub-line DRO while DRO was much more sensitive to AZD6244 than A375.

We have identified specific oncogenic pathways preferentially activated in BRAF-mutated-melanoma cells and a pathway pattern that predicts resistance of BRAF-mutated melanoma to BRAF/MEK inhibitors, providing novel clinical implications for melanoma therapy.

In one embodiment, a method comprises (a) testing a sample of BRAF-mutated melanoma cells isolated from a patient and measuring the expression levels of genes expressed in the following oncogenic pathways: TNFα, EGFR, IFNα, hypoxia, IFNγ, STAT3 and Myc; (b) calculating a 7-pathway activation pattern based on the measured expression levels of step (a); and (c) identifying the patient's resistance level to BRAF/MEK inhibitor treatment based on comparison of the calculated 7-pathway activation pattern to a reference. In a specific embodiment, the identification step is performed using a support vector machine algorithm (SVM).

In another embodiment, a method comprises (a) testing a sample of BRAF-mutated melanoma cells isolated from a patient and using a microarray to measure the expression levels of genes expressed in the following oncogenic pathways: TNFα, EGFR, IFNα, hypoxia, IFNγ, STAT3 and Myc; (b) calculating a 7-pathway activation pattern based on the measured expression levels of step (a), using a SVM algorithm; and (c) identifying the patient's resistance level to BRAF/MEK inhibitor treatment based on comparison of the calculated 7-pathway activation pattern to a reference. The present invention also provides a method comprising (a) testing a sample of BRAF-mutated melanoma cells isolated from a patient at a first time point and measuring the expression levels of genes expressed in the following oncogenic pathways: TNFα, EGFR, IFNα, hypoxia, IFNγ, STAT3 and Myc; (b) calculating a first 7-pathway activation pattern based on the measured expression levels of step (a); (c) testing a sample of BRAF-mutated melanoma cells from the same patient at a second time point and measuring the expression levels of genes expressed in the oncogenic pathways recited in step (a); (d) calculating a second 7-pathway activation pattern based on the measured expression levels of step (c); and (e) identifying the patient's resistance level to BRAF/MEK inhibitor treatment based on comparison of the first 7-pathway activation pattern, second 7-pathway activation pattern, and a reference.

In another aspect, the present invention provides methods for treating BRAF-associated melanoma cancer in a patient. In one embodiment, a method comprises the steps of (a) testing a sample of BRAF-mutated melanoma cells isolated from the patient and measuring the expression levels of genes expressed in the following oncogenic pathways: TNFα, EGFR, IFNα, hypoxia, IFNγ, STAT3 and Myc; (b) calculating a 7-pathway activation pattern based on the measured expression levels of step (a); and (c) treating the patient with a BRAF/MEK inhibitor if the calculated 7-pathway activation pattern corresponds to a reference pattern that correlates with sensitivity to BRAF/MEK inhibitor treatment.

In particular embodiments, the BRAF/MEK inhibitor comprises dabrafenib, trametinib, or combinations thereof. Additional BRAF/MEK inhibitors include, but are not limited to, sorafenib, vemurafenib, selumetinib, binimetinib, PD-325901, and cobimetinib.

In another aspect, the present invention provides methods for predicting resistance to BRAF/MEK inhibitors. In one embodiment, a method for predicting resistance to BRAF/MEK inhibitors in a melanoma cancer patient comprises the steps of (a) measuring gene expression in a melanoma cell isolated from the patient to identify activity in the TNFα, EGFR, IFNα, hypoxia, IFNγ and STAT 3 oncogenic pathways; and (b) predicting resistance to BRAF/MEK inhibitors in the melanoma cancer patient if step (a) identifies low activity in the MYC pathway and high activities in the TNFα, EGFR, IFNα, hypoxia, IFNγ and STAT3 pathways. In another aspect, the present invention provides methods for treating melanoma cancer patients. In one embodiment, a method for treating melanoma cancer in a patient comprises the step administering a BRAF/MEK inhibitor to a melanoma patient not having (a) low activity in the MYC pathway; and (b) high activities in the TNFα, EGFR, IFNα, hypoxia, IFNγ and STAT3 pathways. In certain embodiments, the patient has a BRAF mutation associated melanoma. In particular embodiments, a support vector machine algorithm is used to predict resistance.

DETAILED DESCRIPTION OF THE INVENTION

Figure 1:
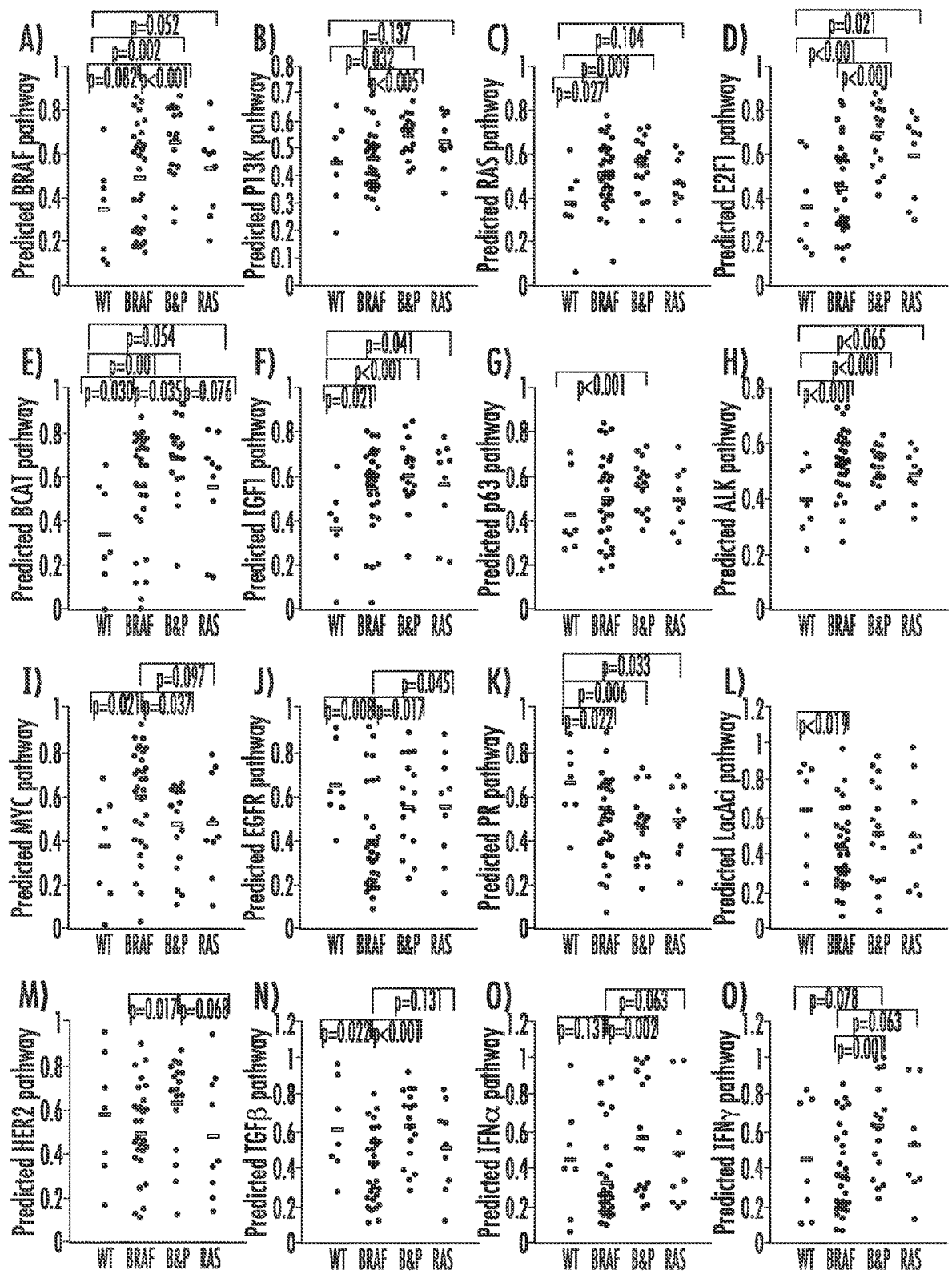
FIG. 1. Activities of multiple cancer-related pathways were associated with specific genetic alterations in melanoma cells. WT: Cell lines did not harbor genetic alterations of BRAF, PTEN, PI3K and RAS (n=7); BRAF: Cells carried BRAF mutation alone (n=30); B&P: cells carried BRAF mutation and PTEN deletion/mutation or PI3K mutation (n=17); RAS: cells carried RAS mutation alone (n=9). Only the pathways that were significantly differently (p≤0.025, randomization test) expressed at least in one pairwise comparison among the 4 groups are shown. Each point represents one cell line, and the average value for each group is shown by a horizontal bar.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention. Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about."

"Optional" or "optionally" means that the subsequently described event or circumstance can or cannot occur, and that the description includes instances where the event or circumstance occurs and instances where it does not.

The terms "patient," "individual," or "subject" are used interchangeably herein, and refer to a mammal, particularly, a human. The patient may have a mild, intermediate or severe disease or condition. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates. In particular, the term also includes mammals diagnosed with a BRAF-mediated disease, disorder or condition. By "normal subject" is meant an individual who does not have cancer as well as an individual who has increased susceptibility for developing a cancer.

As used herein, the term "comparing" refers to making an assessment of how the pathway activation pattern in a sample from a subject relates to the pathway activation pattern in a standard or control sample. For example, "comparing" may refer to assessing whether the pathway activation pattern in a sample from a subject is the same as, more or less than, or different from the pathway activation pattern in a standard or control sample. More specifically, the term may refer to assessing whether the pathway activation pattern in a sample from a subject is the same as, more or less than, different from or otherwise corresponds (or not) to predefined pathway activation patterns that correspond to, for example, a subject sensitive or resistant to a melanoma treatment. In a specific embodiment, the term "comparing" refers to assessing whether the pathway activation pattern in a sample from a subject is the same as, more or less than, different from other otherwise correspond (or not) to a pathway activation pattern in a control sample (e.g., predefined levels that correlate to subject sensitive or resistant to a melanoma treatment).

As used herein, the terms "indicates" or "correlates" (or "indicating" or "correlating," or "indication" or "correlation," depending on the context) in reference to a pathway activation pattern may mean that the subject is sensitive or resistant to BRAF/MEK inhibitor treatment. In certain embodiments, "indicating," or "correlating," as used according to the present invention, may be by any linear or non-linear method of quantifying the relationship between pathway activation patterns to a standard, control or comparative value for the prediction of resistance or sensitivity to particular melanoma treatments.

The terms "measuring" and "determining" are used interchangeably throughout, and refer to methods which include obtaining a subject sample and/or detecting the expression level of gene(s) involved in a particular pathway. In one embodiment, the terms refer to obtaining a subject sample and detecting the expression level of gene(s) involved in a particular pathway. In another embodiment, the terms "measuring" and "determining" mean detecting the expression level of gene(s) involved in a particular pathway. Measuring can be accomplished by methods known in the art and those further described herein including, but not limited to, polymerase chain reaction. The term "measuring" is also used interchangeably throughout with the term "detecting."

The terms "sample," "subject sample," "biological sample," and the like, encompass a variety of sample types obtained from a patient, individual, or subject and can be used in a diagnostic or monitoring assay. The subject sample may be obtained from a healthy subject, a subject suspected to be at risk for melanoma (family history) or a subject diagnosed with melanoma (e.g., BRAF-associated melanoma). Moreover, a sample obtained from a subject can be divided and only a portion may be used for testing. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as a "reference," "appropriate control" or a "control sample." A "reference," "suitable control," "appropriate control" or a "control sample" is any control or standard familiar to one of ordinary skill in the art useful for comparison purposes. In one embodiment, a "suitable control" or "appropriate control" is a pathway activation pattern determined in a cell or subject, e.g., a control cell or subject, exhibiting, for example, sensitivity to a melanoma treatment. In a further embodiment, a "suitable control" or "appropriate control" is a predefined pathway activation pattern. A "suitable control" can be a pathway activation pattern that correlates to sensitivity or resistance to melanoma treatment, to which a subject sample can then be compared.

The term "inhibitor" is a type of modulator and is used interchangeably with the term "antagonist." The term "inhibitor" includes any type of molecule or agent that directly or indirectly inhibits the expression or activity of a target gene or protein. An inhibitor can be any type of compound, such as a small molecule, antibody or antisense compound. In certain embodiments, the target gene or protein is BRAF. The term also includes agents that have activity in addition to BRAF inhibitory activity. Examples of BRAF inhibitors include Sorafenib (Bay 43-9006, Nexavar) and Vemurafenib (PLX4032), BDC-0879, PLX-4720, Dabrafenib (Tafinlar), and LGX818. In still another embodiment, the target gene or protein is MEK, a protein downstream BRAF in the BRAF/MEK/MAP kinase pathway. Examples of MEK inhibitors include trametinib, selumetinib (AZD6244), trametinib, CI1040, PD0325901, RDEA119 (refametinib, BAY 869766). In still another embodiment, the combination use of BRAF and MEK inhibitors targeting all genes or proteins is more effective.

Activities of Multiple Cancer-Related Pathways are Associated with BRAF Mutation and Predict the Resistance to BRAF/MEK Inhibitors in Melanoma Cells Several BRAF/MEK signaling pathway inhibitors, including inhibitors selectively against BRAFV600E or its downstream molecular MEK, have shown prominent effects in melanoma patients in recent clinical trials. One of the major clinical obstacles in this molecular-targeted therapy is, however, the commonly seen innate drug resistance. Thus, novel treatment strategies and biomarkers for prediction of such drug resistance are urgently needed to improve the response rates and the duration of clinical benefit. In this context, it is interesting that several molecular abnormalities, such as the activation of hepatocyte growth factor (HGF)/MET signaling, have been recently found to be associated with the innate resistance to BRAF/MEK signaling inhibitors in a small range of BRAF-mutated cancer cells. Identification of more universal biomarkers for predicting drug resistance is in need to facilitate the development of novel strategies tacking the drug resistance issues in melanoma.

We analyzed the activities of 24 cancer-related pathways in BRAFV600E melanoma cells using BinReg approach. Seven pathways, including TNFα, EGFR, IFNα, hypoxia, IFNγ, STAT3 and MYC, were significantly differently expressed in AZD6244 (a MEK inhibitor)-resistant compared with responsive melanoma cells. A SVM classifier built on this 7-pathway activation pattern correctly predicted the response of 10 BRAF-mutated melanoma cell lines to the MEK inhibitor AZD6244 in our experiments, indicating that this pathway pattern can be used to predict the resistance of BRAF-mutated melanoma cells to BRAF/MEK signaling inhibitors.

We also identified patterns of the activation of multiple oncogenic pathways that occurred preferentially in BRAF-mutated melanoma cells, especially in cells carrying both BRAF and PTEN abnormalities, which uniquely linked the molecular pathologies and clinical features of melanoma. This data not only shed new lights on the molecular pathologies of melanoma, but also suggested potential targets for melanoma therapy.

Materials and Methods

Melanoma cells and cell culture. Melanoma cell lines A375, COLO829, SK-MEL-1, SK-MEL-3, and SK-MEL-24 were purchased from American Type Culture Collection (ATCC), cell lines Malme-3M, UACC62, RPMI-7951, SK-MEL-5 and SK-MEL-28 were purchased from National Cancer Institute (NCI). DRO, a sub-line derived from melanoma cell A375, was a kind gift from Dr. Guy J. F. Juillard (University of California-Los Angeles School of Medicine, CA). All these cell lines harbor BRAFV600E mutation, which we confirmed by genomic DNA sequencing (data not shown). Cells were cultured and maintained following the protocols recommended by ATCC or NCI.

Microarray datasets. The raw microarray data of all the datasets used in this study as listed Table 2, except the expression data for the A375/DRO syngenic cell lines, were downloaded from Gene Expression Omnibus (GEO) and normalized by Microarray Suite 5.0 (MAS5.0) and/or Robust Multi-array Average (RMA) approach respectively in R environment (http://www.r-project.org).

Pathway Signatures and Pathway Activity Prediction

The generation of pathway signatures and prediction of pathway activity of individual sample were performed using BinReg tool as described previously in detail by Gatza et al (1). In this approach, the gene expression patterns of two training sample sets (for example, pathway 'on' and pathway 'off') are compared, and the pathway-specific informative genes were identified. Principal components were then used to compute weights for each of these genes such that the weighted average of expression levels showed a clear ability to distinguish the pathway 'on' and 'off' group. Binary regression on the principal components is then applied to an unknown test sample, producing estimated relative probability (score) of pathway activity, which can be considered as a correlative measure of in vivo pathway activity.

The training datasets and signatures for the 24 pathways analyzed in this study, except for BRAF, ALK and IGF1 pathways, were previously reported by Gatza et al (1, 2). As suggested by the authors (1, 2), MAS5.0 normalized gene expression data was used for prediction of AKT, MYC, p53, p63, RAS, STAT3 and TNFα pathway activities, while RMA normalized data was used for Wnt/β-catenin (BCAT), E2F1, EGFR, estrogen receptor (ER), GlucoseDeprivation (GluDepr), HER2, Hypoxia, IFNα, IFNγ, LacticAcidosis (LacAcid), PI3K, progesterone receptor (PR), SRC and TGFβ pathways.

Prediction of AZD6244-Resistant Melanoma Cells by Support Vector Machine (SVM) Algorithm LIBSVM (version 3.0), a freely available software package (17), was employed for learning and prediction process in this study. Radial basis function kernel (RBF) and 5-fold cross validation were chosen to build SVM classifier, and best values for model parameter c and γ were obtained by a grid-search method. The pathway signatures of the 46 BRAF-mutated melanoma cell lines from Johansson dataset (GSE7127) (18) were used as training set, while those of 10 melanoma cell lines from Barretina dataset (GSE36133) (19), including A375, COLO829, SK-MEL-1, SK-MEL-3, SK-MEL-5, SK-MEL-24, SK-MEL-28, Malme-3M, UACC62 and RPMI7951, were used as test set. We choose these 10 cell lines because our laboratory has stocks of these cell lines and thus the results obtained by bioinformatics analysis on these lines could be further examined by experimental approaches. Both the training and test datasets were derived from same microarray platform, making the gene expression data comparable cross arrays. The 7 pathways, which showed significantly different activity (randomization test, one-tail, $p \leq 0.025$) between AZD6244-responsive and resistant BRAF-mutated melanoma cell lines from Johansson dataset, were chosen as feature pathways to build prediction model. To search the best pathway combinations for prediction of drug resistant cells, we further use the SVM-based Recursive Feature Elimination (RFE-SVM) to rank the 7 pathways basing on their weight vector values. The RFE-SVM algorithm is a weight-based feature selection method that generates the ranking of features using backward feature elimination (20). The features are eliminated according to a criterion related to their support to the discrimination function. In our study RBF kernel was applied as kernel function for RFE-SVM analysis and the ranking coefficient is defined as:

$$\text{rank}(i) = (1/2)\alpha^T Q \alpha - (1/2)\alpha^T Q(-i)\alpha$$

where $H_{ij} = K(x_i, x_j)$, K is the kernel function, α is the Lagrange multiplier, and (−i) means that the feature i has been removed.

Statistics

Differences in mean pathway activities between two tumor groups were evaluated using randomization test as we described previously (25). Briefly, the prediction values of one specific pathway activity in two tumor groups (for example, melanoma with BRAF mutation and melanoma with RAS mutation) were resampled without replacement for 50,000 times, and the delta value (difference between the average values of the two groups) was computed each time. The incidence (T) of which the random delta values were higher than the actual delta value (if the actual delta value >0), or less than the actual delta value (if the actual delta value<0), was counted and the p value for an individual pathways was obtained by dividing T with 50,000 (T/50000). A p-value of $\leq 0.025$ was set as statistical significance as the test is a one-tail test.

Results

Generation of Pathway Signatures for BRAF, IGF1 and ALK Signaling Pathways

Figure 7:
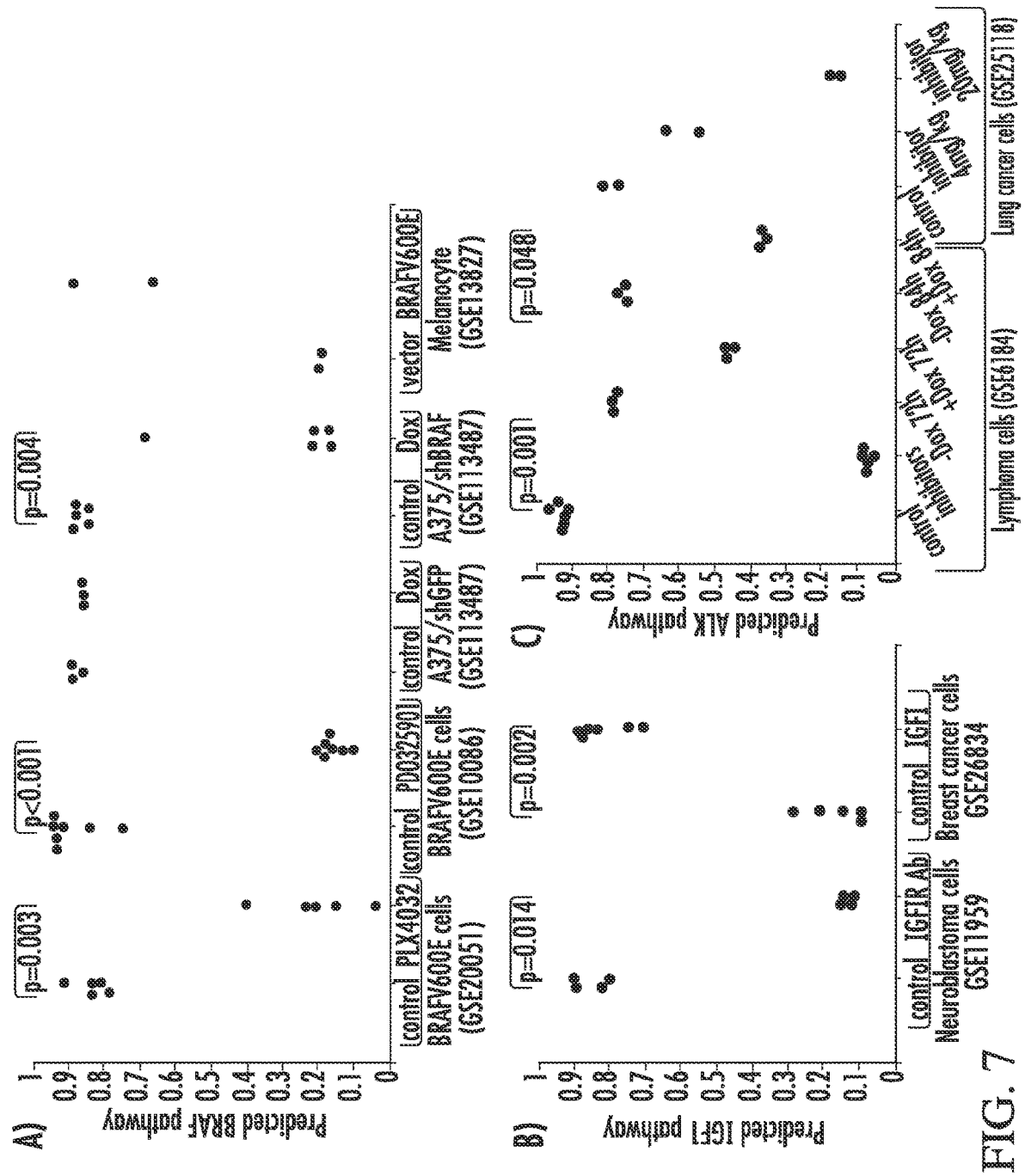
FIG. 7. Validation of signatures of BRAF, IGF1 and ALK pathways. A) BRAF pathway signature. The gene expression data of 5 BRAFV600E melanoma cell lines treated with or without 250 nM BRAFV600E inhibitor PLX4032 (GSE20051) was used as training set to generate BRAF pathway signature. The signature was then applied for prediction of the BRAF pathway activity (predicted probability) of the training set and the following validation sets: two BRAFV600E colon cancer lines and five BRAFV600E melanoma cell lines treated with or without MEK inhibitor PD0325901 (GSE10086), BRAFV600E melanoma cell line A375 with Dox-inducible BRAF knock-down (GSE13487), and melanocyte with forced expression of BRAFV600E (GSE13827). A375/shGFP: Dox-inducible GFP knock-down; A375/shBRAF: Dox-inducible BRAF knock-down. B) IGF1 pathway signature. The gene expression data of human neuroblastoma cell line SK-N-AS treated with or without anti-IGF1R antibody 10H5 (GSE11959) was used as training set to generate IGF1 pathway signature. The signature was then applied for prediction of the IGF1 pathway activity of the training set and human breast cancer cell line MCF7 treated with or without IGF1 (GSE26834). C) ALK pathway signature. The gene expression data of anaplastic large cell lymphoma cell line TS treated with or without ALK inhibitors A2 or A3 (GSE6184) was used as training set to generate ALK pathway signature. The signature was then applied for prediction of the ALK pathway activity of the training set and the following validation sets: TS cells treated with Dox to induced ALK knock-down by shRNA for 72 h or 84 h (GSE6184), and xenograft tumors (formed by lung cancer cell line-NCI-H2228) treated with 4 mg/kg or 20 mg/kg ALK inhibitor CH5424802 (GSE25118). −Dox: cells were treated without Dox, +Dox: cells were treated with Dox to induce ALK knock-down by shRNA for 72 h or 84 h as indicated. Randomization test was used for statistical analysis of pathway activities between two groups of samples.

A total of 24 cancer-related pathways were analyzed in this study. The signatures for 21 of the 24 pathways were reported previously (7, 8, 10). The signatures for the rest 3 pathways, including BRAF, IGF1 and ALK pathways, were generated in this study based on the gene expression datasets published in GEO as described in Supplementary Materials and Methods. As shown in FIG. 7, the signatures generated by training set were able to predict well the pathway activities of samples from both training and test sets.

Figure 8:
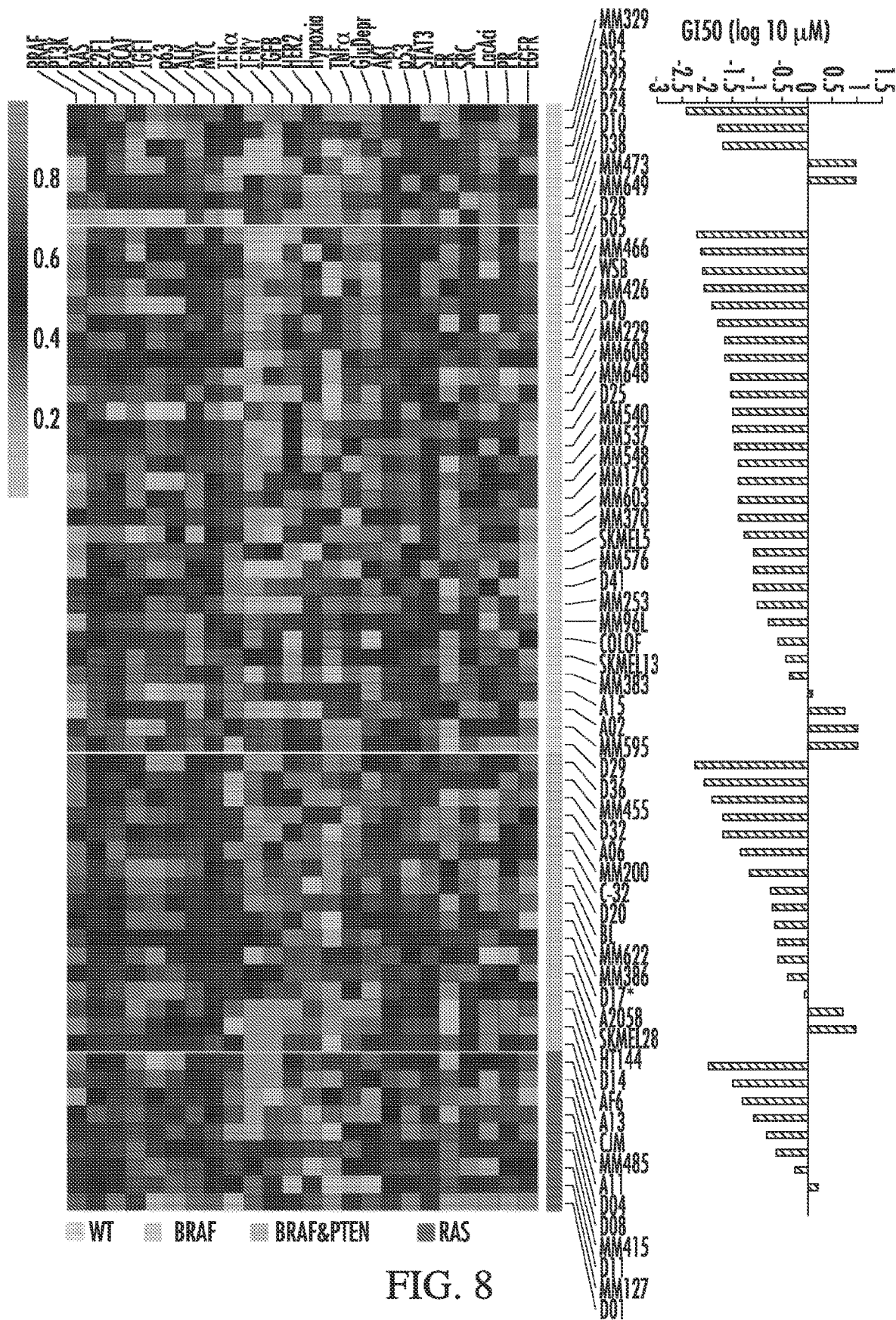
FIG. 8. Heatmap of cancer-related pathway activities in melanoma cells with different genetic alterations (Johansson dataset). Each colored cell in the heatmap represents the predicted possibility of one pathway in the corresponding cell line. The site bar with 4 different colors represents 4 groups of samples harboring different genetic alterations as indicated. The 3 white lines separate the heatmap into 4 parts that correspond to the 4 groups of samples respectively. The GI50 data for these cell lines, as shown in the column chart at the right of the figure, are from ref (21). The columns for D10, D38, A13 and D01 cell lines were missing as the GI50 values for these lines were not available. The cell line D17, which was marked with a star, harbor PIK3CA mutation and is classified into BRAF&PTEN class.

Activation of Multiple Oncogenic Pathways Preferentially Occurring in BRAF-Mutated Melanoma Cells, Particularly in Cells with Both BRAF and PTEN Alterations The 24 pathway activities in 63 melanoma cell lines were analyzed based on the gene expression data of the Johansson dataset (GSE7127) (12) (FIG. 8). According to the genetic alterations of BRAF, RAS, PTEN and PIK3CA in the 63 cell lines (12), we divided the 63 lines into 4 groups. Group WT (wild-type) included 7 cell lines that did not harbor any mutations in the 4 genes; group BRAF included 30 lines carrying BRAF mutation alone; group BRAF&PTEN (B&P) included 16 lines carrying BRAF mutation and PTEN deletion/mutation and one line carrying BRAF and PIK3CA mutations; the rest 9 cell lines with RAS mutation alone were classified as group RAS.

Sixteen of the 24 pathways were significantly differently expressed at least in one pairwise comparison among the 4 groups ($p \leq 0.025$, randomization test) (FIG. 1). As expected, the cells with BRAF or RAS mutations showed higher activity in the BRAF and RAS signaling pathways, while cells with PTEN, PIK3CA or RAS alterations showed higher activity in the PI3K pathway (FIG. 1A-C). Compared with group WT, melanoma cells with any of the genetic alterations in the four genes also had higher activities in another 6 cancer-related pathways, including E2F1, Wnt/β-catenin (BCAT), IGF1, ALK, MYC and p63 signaling pathways (FIG. 1D-I), which were all putative oncogenic pathways (13-16) except for the p63 pathway that is uncertain (17). By contrast, cells in group WT had higher activity than the other 3 groups only in 3 cancer-related pathways, including EGFR, progesterone receptor (PR) and LacticAcidosis (LacAcid) pathways (FIG. 1J-L).

Interestingly, the cells in group BRAF&PTEN showed higher activities than cells in group BRAF in 13 of the 16 cancer-related pathways (FIG. 1A-G, J, L-P), of which 8 pathways had the p-values <0.025 (FIG. 1A, B, D, J, M-P). Among the 13 pathways, 8 pathways, including BRAF, RAS, PI3K, E2F1, BCAT, IGF1, EGFR, and HER2, were well-known oncogenic pathways, and the rest pathways, including p63, TGFβ, IFNα, and IFNγ, had cellular context-dependent oncogenic roles (3, 13-16, 18, 19).

Figure 9:
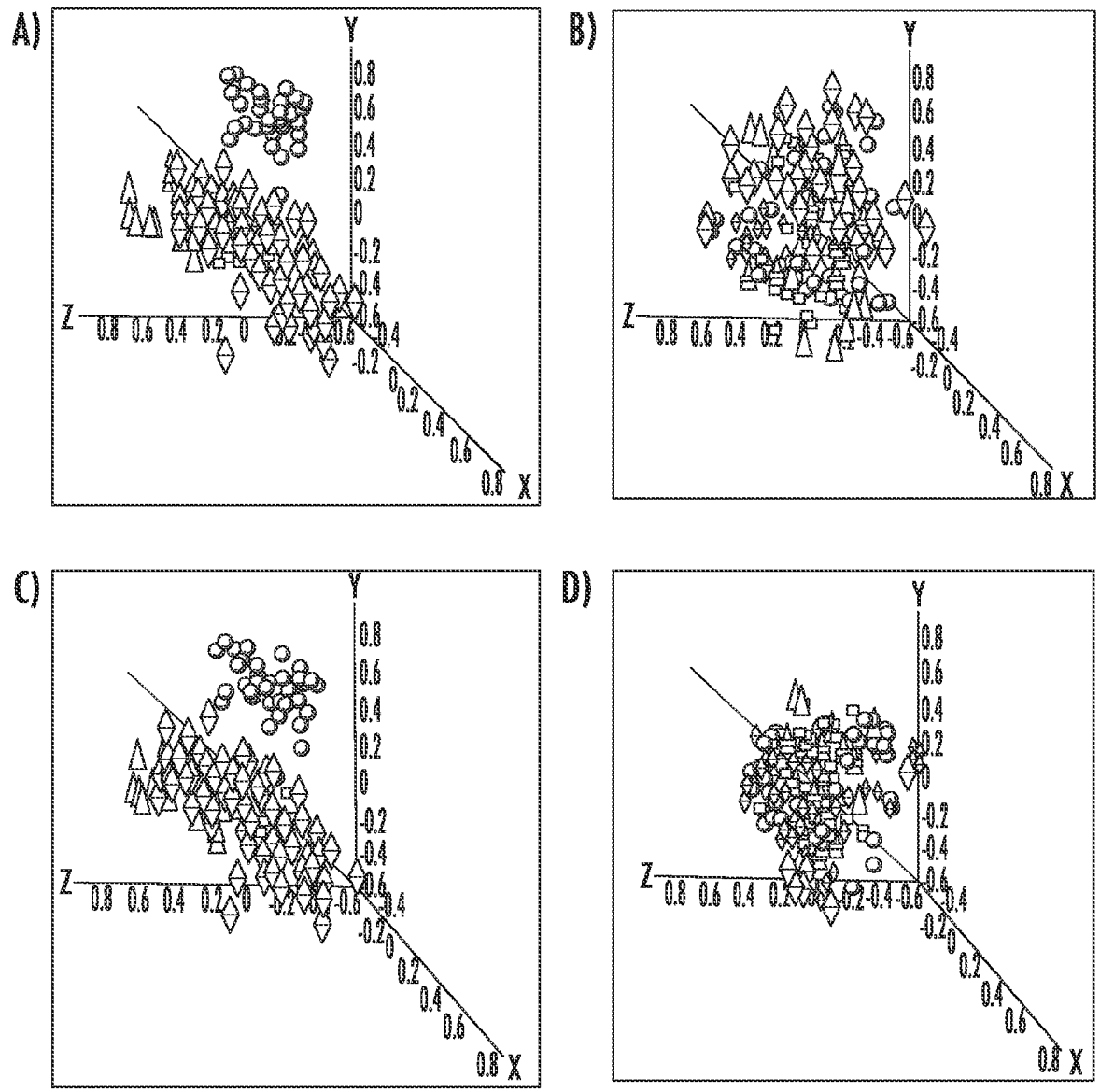
FIG. 9. Dataset-specific biases were removed from gene expression datasets merged by ComBat program. A) Principal component analysis (PCA) of 5 independently generated melanoma datasets that were normalized by RMA approach. The samples from one individual array were indicated by markers with same shape and color. B) PCA of the 5 RMA-normalized datasets merged with ComBat program. The dataset-specific biases were successfully removed by ComBat since the samples from different arrays in the merged dataset were well intermixed. C) PCA of 5 independently generated melanoma datasets that were normalized by MAS5.0 approach. D) PCA of the 5 MAS5.0-normalized datasets merged with ComBat program. The dataset-specific biases were successfully removed by ComBat.
Figure 10A:
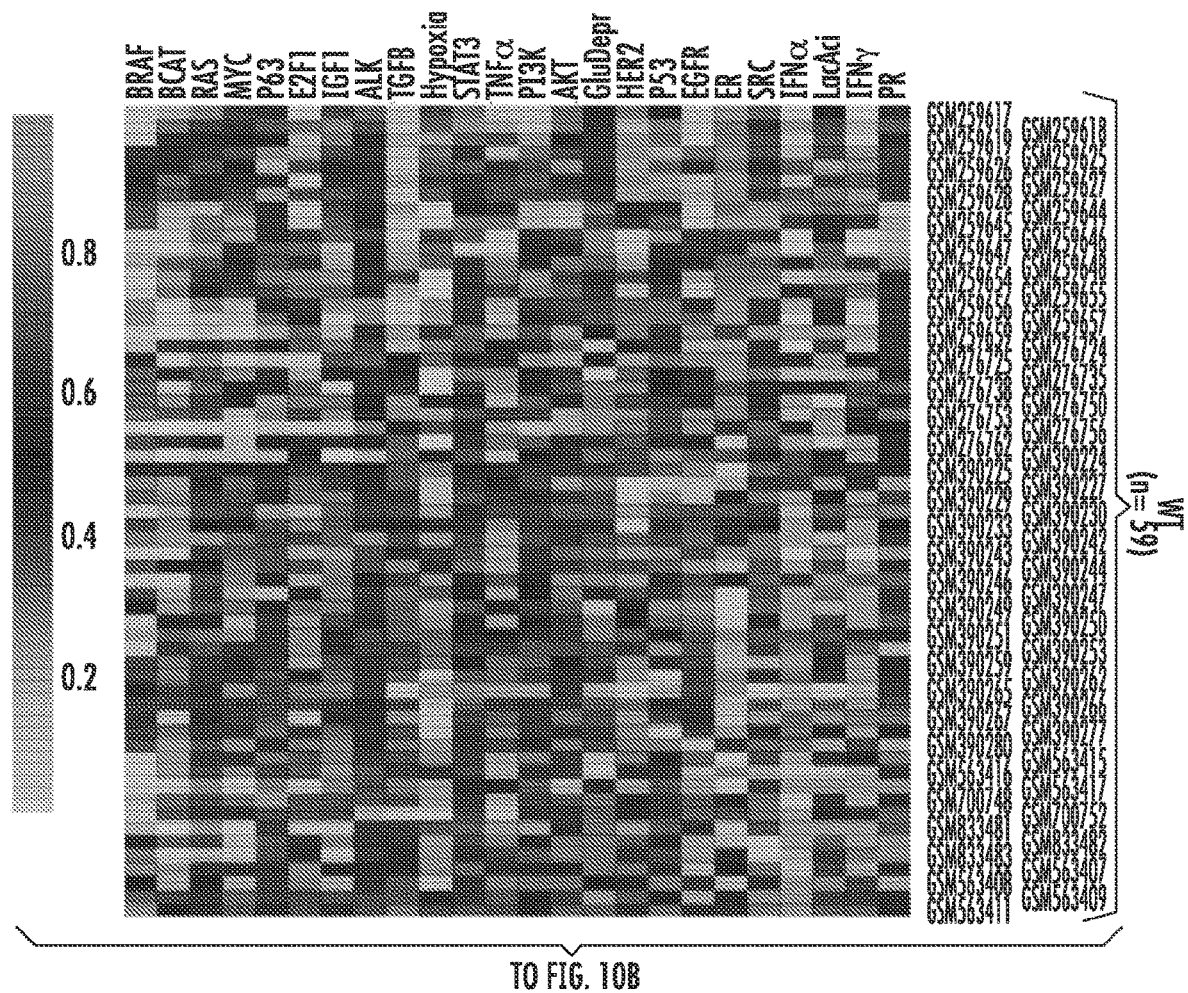
FIG. 10. Heatmap of cancer-related pathway activities in melanoma cells with different genetic alterations (merged dataset). Each colored cell in the heatmap represents the predicted possibility of one pathway in the corresponding cell line. The 169 melanoma samples from 5 melanoma microarray datasets (GSE10282, GSE10916, GSE15605, GSE22787 and GSE33728) were classified into 3 groups according to their genotypes in BRAF and RAS. The sample names listed at the right side of heatmap are the accession numbers of these samples in GEO database. The two white lines separate the heatmap into three parts that correspond to the 3 groups of samples respectively.
Figure 10B:
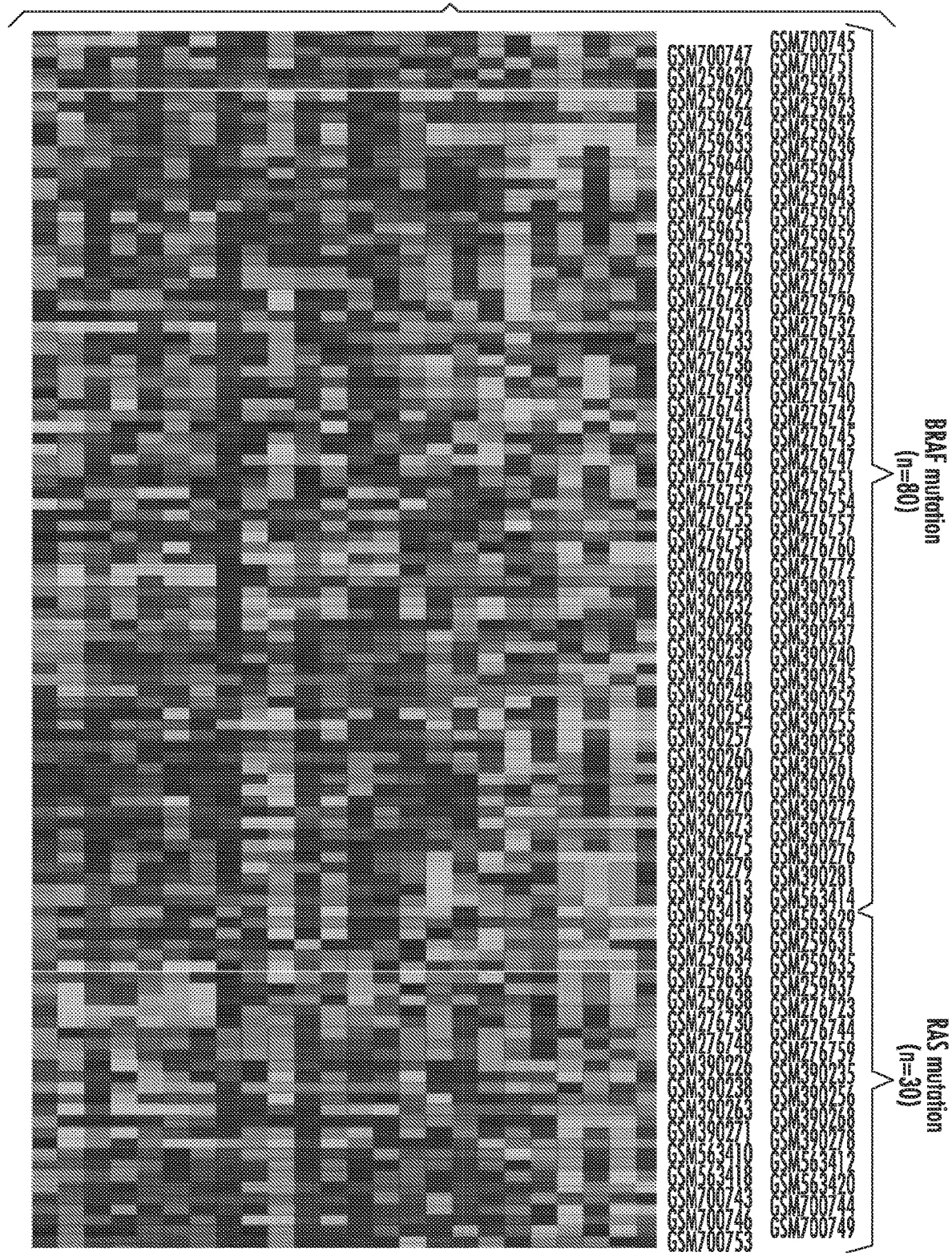

Analysis on 5 Additional Microarray Datasets Confirmed the Activation of Multiple Oncogenic Pathways in BRAF-Mutated Melanoma We further analyzed the 24 pathways in one large dataset that was merged from 5 microarray datasets. ComBat program (20) was used to merge these datasets to remove dataset-specific biases (FIG. 9). Among the 196 samples of the 5 datasets, 169 melanoma samples had confirmed BRAF and RAS mutation information (FIG. 10). As the genetic alteration of PTEN or PIK3 CA were not available for the merged dataset, to make the results comparable between this merged dataset and the Johansson dataset, we combined the BRAF and BRAF&PTEN groups in the Johansson dataset into one group (n=37) and analyzed the pathway activity difference between the combined group and group WT.

Figure 2:
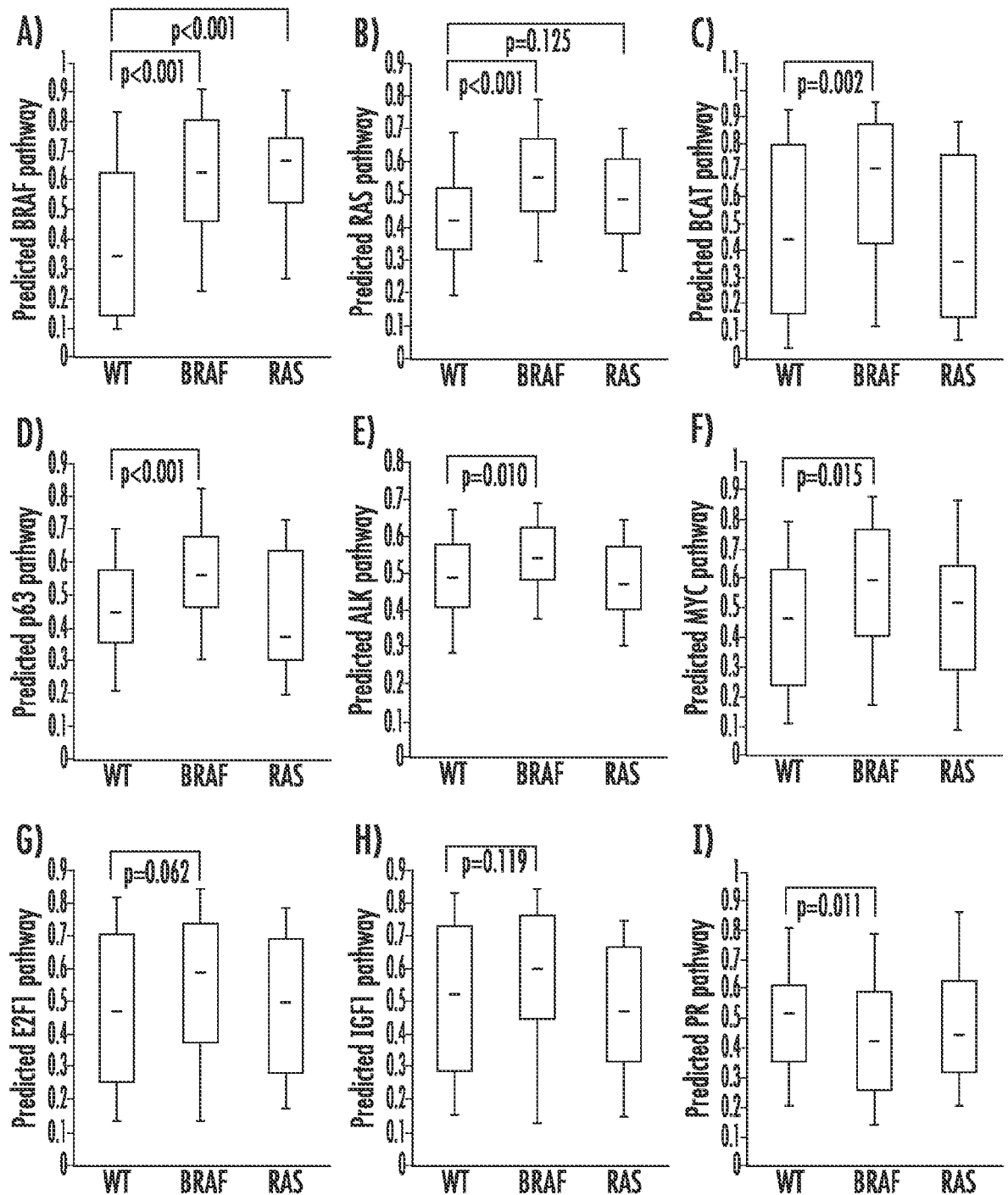
FIG. 2. Analysis on 5 additional microarray datasets confirmed the activation of multiple oncogenic pathways in BRAF-mutated melanoma. Box-Whisker plots of individual oncogenic pathways. The box-plot shows the five statistics (the lower whisker is 5% minimum, the lower box part is the 25th percentile, the solid line in the box presents the median, the upper box part is 75th percentile, and the upper whisker is 95% maximum). Randomization test was used to calculate the p-values for the pairwise comparison of pathway activities among the three groups of melanoma, i.e., WT (n=59), BRAF mutation (n=80), and RAS mutation (n=30) groups.

As shown in Table 1, a total of 7 pathways were significantly differently expressed between WT and BRAF-mutated cells in either the Johansson dataset or the merged dataset (p≤0.025, randomization test). Among these 7 pathways, BRAF, RAS, BCAT and ALK pathways were upregulated in BRAF-mutated cells while PR pathway was upregulated in WT cells in both datasets (FIG. 1A, C, E, H, K and FIG. 2A-C, E, I). P63 and MYC pathways showed a significantly higher activity in BRAF-mutated cells in the merged dataset (FIG. 2D, F) and a statistically non-significant higher trend in the Johansson dataset (FIG. 1G, I). The E2F1 and IGF1 pathways showed a significantly higher activity in BRAF-mutated cells in the Johansson dataset (FIG. 1D, F; Table 1) and a statistically non-significant higher trend in the merged dataset (FIG. 2 G, H). These highly consistent results between the two datasets strengthened further that BRAF mutation was associated with activation of multiple oncogenic signaling pathways, including RAS, BCAT, ALK, E2F1, IGF1, MYC and p63 pathways, in melanoma cells.

Only the E2F1 pathway in the Johansson dataset and the BRAF pathway in the merged dataset showed significantly different activities between RAS-mutated and WT cells (FIG. 1D, FIG. 2A). These 2 pathways, as well as RAS, MYC and PR pathways, showed the same pattern between RAS-mutated and WT cells in both datasets (FIG. 1C, I, K, and FIG. 2B, F, I). The patterns of several other pathways, such as BCAT, IGF1, p63 and ALK, were, however, not consistent between the 2 datasets (FIG. 1E-H and FIG. 2C-E, H).

Figure 3:
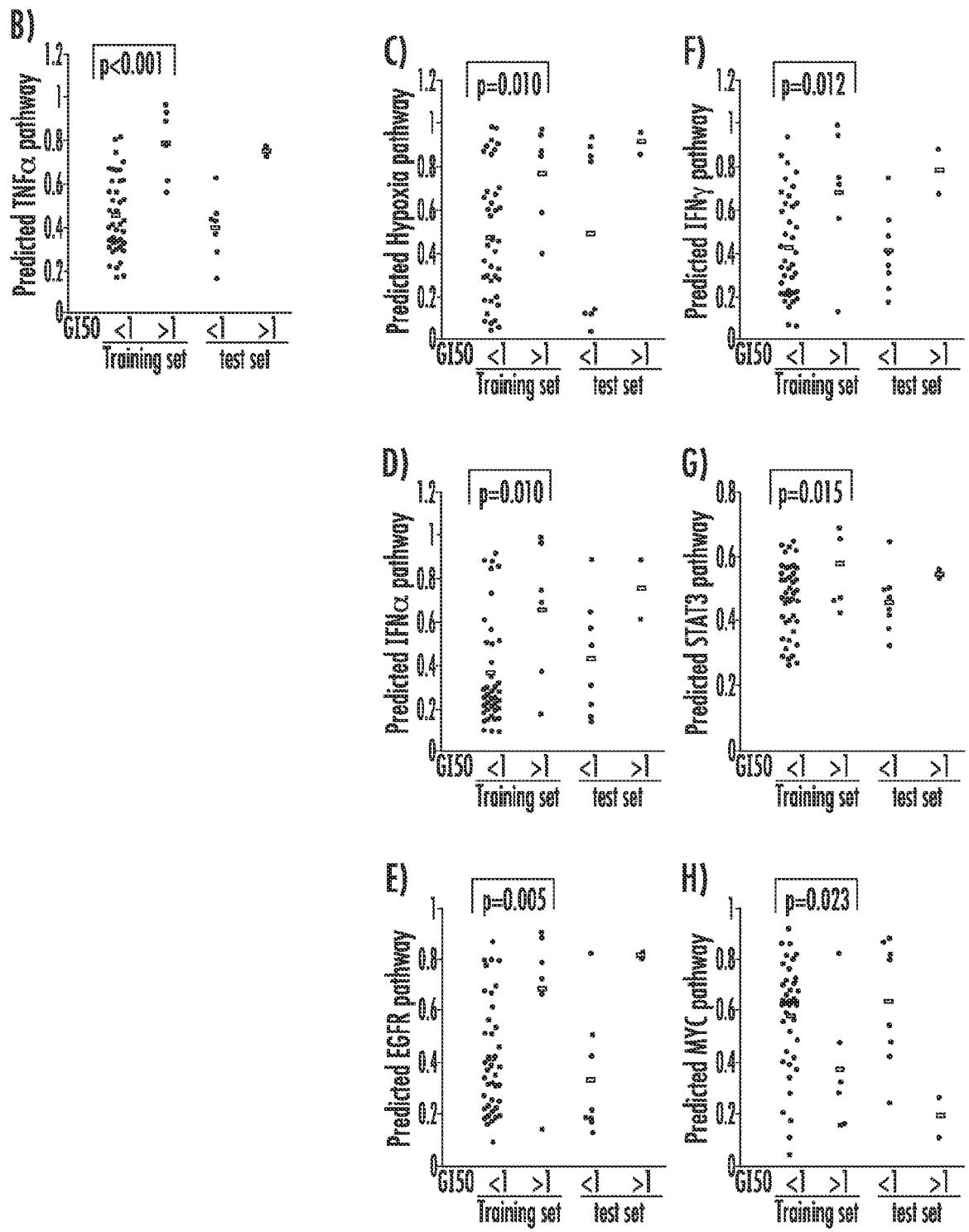
FIG. 3. Identification of a 7-pathway pattern that distinguish AZD6244-resistant and responsive melanoma cells. A) Heatmap of the predicted 24 pathway activities in the 46 melanoma cells with BRAF mutation. The GI50 value of AZD6244 were used to define whether the cells were AZD6244 resistant (>1 μM) or responsive (<1 μM). The pathways that showed statistical significance (p≤0.025, randomization test) in predicted activities between the two groups are highlighted with red color. The GI50 data for these cell lines were from ref (50). B-H) Distribution of the predicted activities of the 7 pathways that were significantly differently expressed between AZD6244-resistant and responsive melanoma cells. Each point represents one cell line, and the average value for each group is shown by a horizontal bar.
Figure 3A:
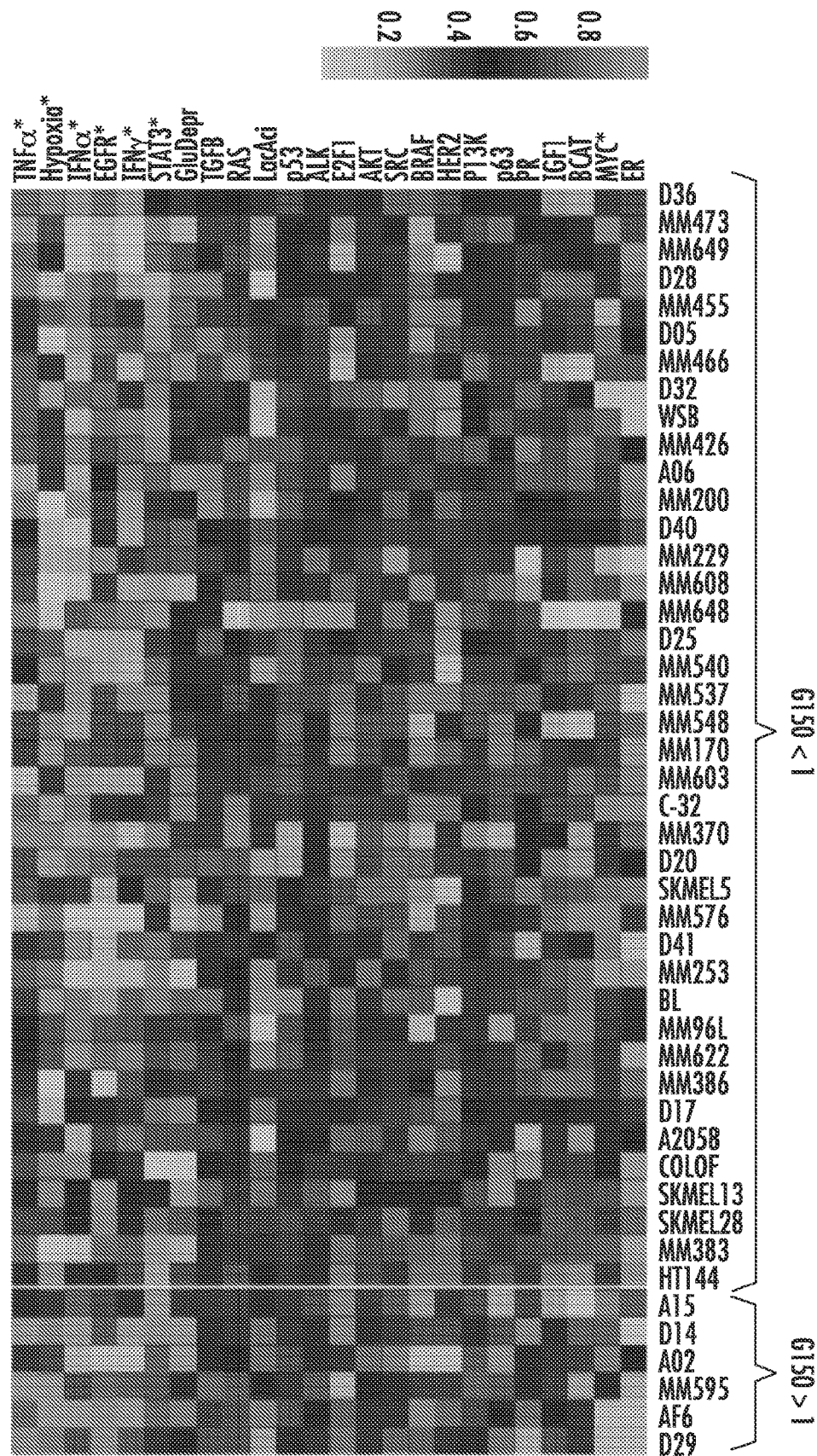

Identification of a Pathway Pattern Associated with AZD6244-Resistance in BRAF-Mutated Melanoma Cells Forty-seven of the 63 melanoma cell lines in the Johansson dataset harbored BRAF mutation. Based on the sensitivity to the MEK inhibitor AZD6244, we divided the 46 of 47 cell lines (GI50 is not available for one BRAF-mutated line) into AZD6244-responsive (GI50<1 μM) and resistant (GI50 value >1 μM) groups (FIG. 3A). Randomization test showed that 7 of the 24 pathways had significantly different activity between these two groups of melanoma cells, including TNFα, EGFR, IFNα, hypoxia, IFNγ and STAT3 pathways (upregulated in AZD6244-resistant cells) and MYC pathway (downregulated in the resistant cells) (FIG. 3). We named this signature profile as the 7-pathway pattern.

Figure 11:
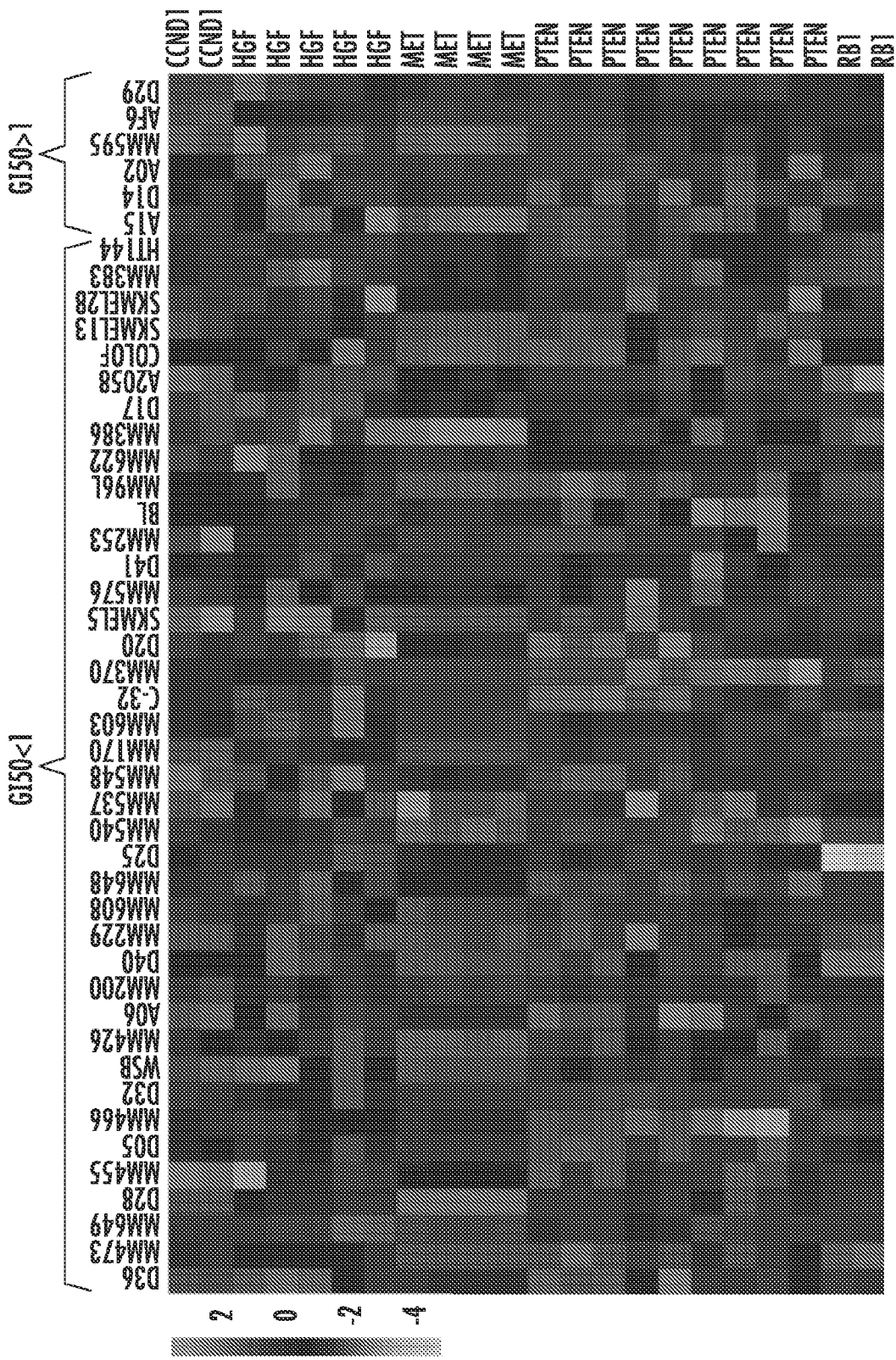
FIG. 11. The relative expression level of CCND1, HGF, MET, PTEN and RB1 in the 46 melanoma cells from training set. The expression data of these 5 genes, which was extracted from RMA-normalized dataset GSE7127, was illustrated by heatmap. Each colored cell in the heatmap represents the relative level of a gene probe in the corresponding cell line.

No difference in the BRAF pathway activity was observed between the two groups of melanoma cells, nor was that in PI3K and Akt pathway activities (FIG. 3A). In fact, 14 of the 16 melanoma cells harboring BRAF mutation and PTEN inactivation were responsive to AZD6244 (FIG. 8). In addition, no difference in the expression level was observed for CCND1, HGF, MET, PTEN and RB1 that could potentially be related with the innate resistance of cancer cells to BRAF/MEK signaling inhibitors (2, 3, 5), suggesting that these genes were not associated with resistance to AZD6244 in these melanoma cells lines (FIG. 11).

Figure 4:
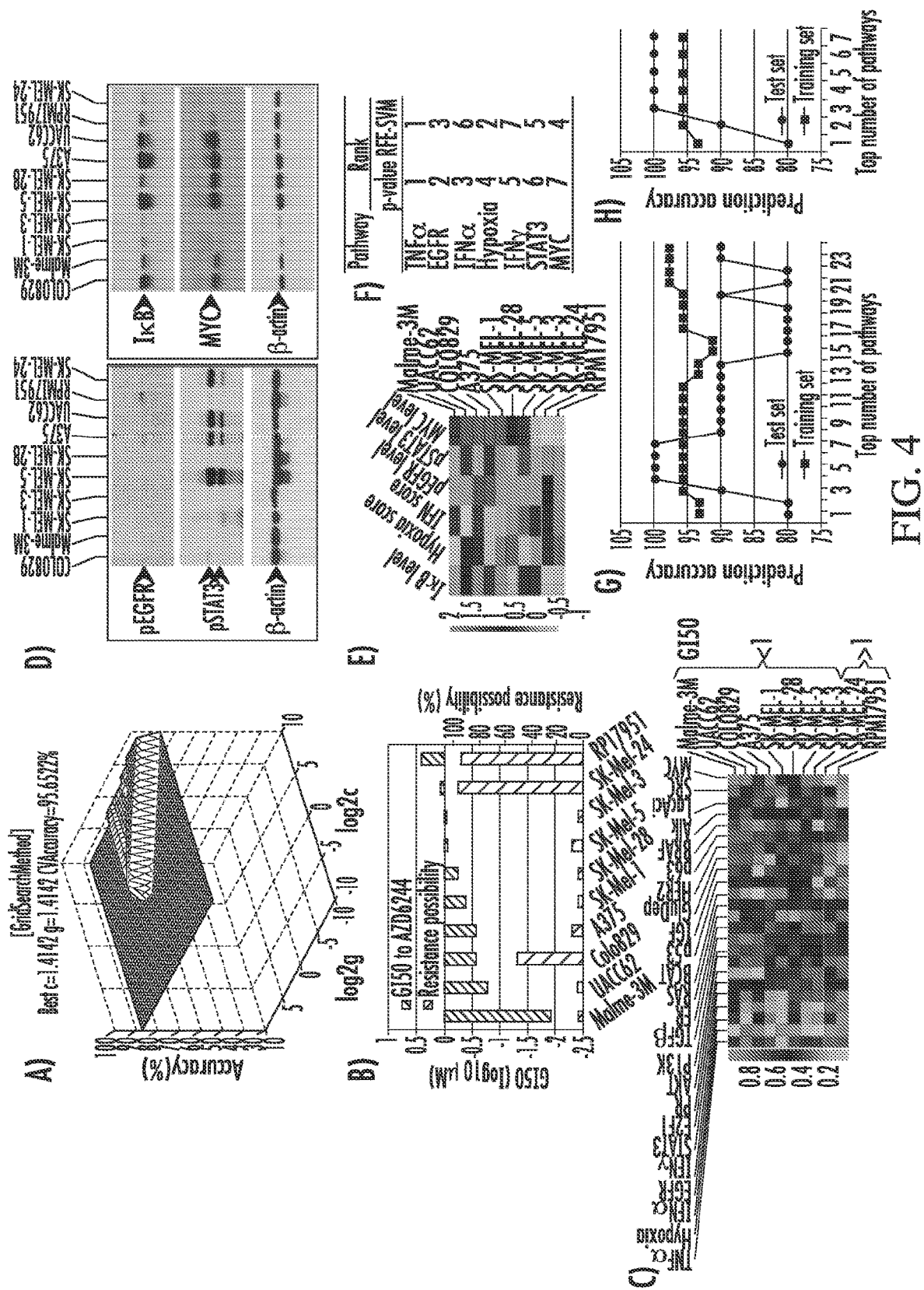
FIG. 4. Prediction of AZD6244 resistance of melanoma cells with SVM classifier based on the 7-pathway pattern. A) Best c and γ values for SVM model were obtained by grid-search approach. B) Prediction of AZD6244 resistance by SVM and experimental validation of the SVM results. The SVM predicted results (possibility as AZD6244 resistance, right y-axis) for 10 melanoma cell lines tested are shown as the yellow columns, and the actual sensitivities of the cell lines to AZD6244 (GI50 values, left y-axis) are shown as the blue columns. By default, the SVM classifier classified the cells with a >50% possibility into the AZD6244-resistant group, while the rest into the AZD6244-responsive group. C) Heatmap of the predicted 24 pathway activities in the 10 melanoma cells from the test dataset. The components (pathways) of the 7-pathway pattern are highlighted in red. D) Western blot analysis of the proteins related to the EGFR, STAT3, TNFα or MYC pathways. The blotting results obtained from the same membrane are boxed together. E) Heatmap of the relative pathway activities obtained by experimental approach. The pathway activities of EGFR, STAT3, IκB and MYC were based on the results in the FIG. 4D, and were calculated as the relative level of corresponding proteins (normalized by β-actin level). Theoretically, the IκB level is negatively correlated with TNFα pathway activities. The pathway activities of the hypoxia and IFN were based on hypoxia and IFN scores that were calculated from the qRT-PCR results (Table 3). F) Pathway ranking list based on their statistical p-values calculated by the randomization test or their weight vector values computed by RFE-SVM. G) Prediction accuracy using different top numbers of pathways (ranking based on the p-values) to build SVM classifier. The pathways ranked from 1st to 7th are listed in FIG. 4F, and pathways ranked from 8th to 24th are estrogen receptor (ER), IGF1, Glucose Deprivation (GluDepr), RAS, BCAT, TGFβ, PR, LacAci, p63, p53, ALK, PI3K, AKT, E2F1, SRC, BRAF, and HER2, respectively. H) Prediction accuracy using different top numbers of pathways (ranking based on RFE-SVM analysis) to build SVM classifier.
Figure 12:
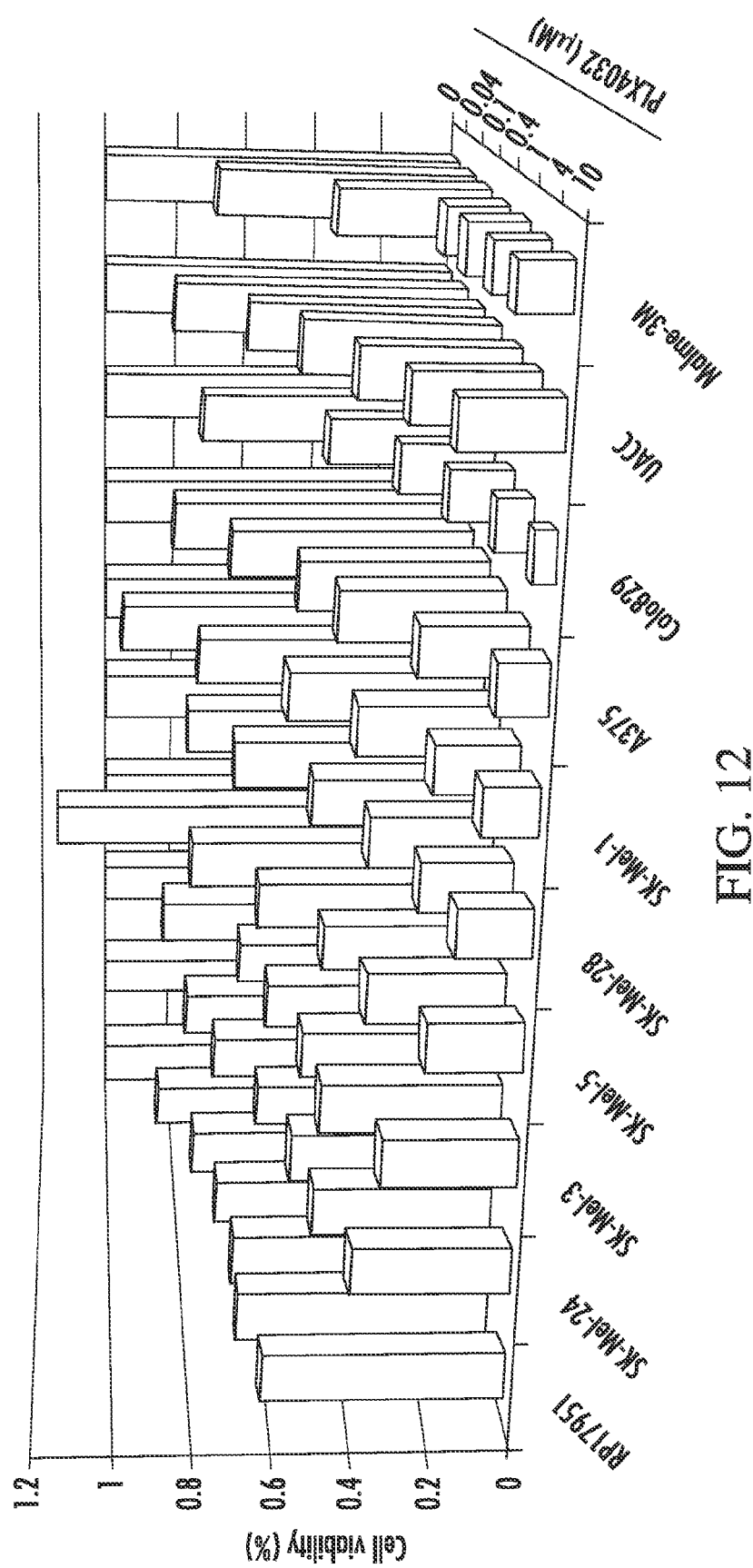
FIG. 12. PLX4032 effects on the proliferation of the 10 melanoma cells from test set. Cells were treated with the indicated concentrations of BRAFV600E inhibitor PLX4032 for 72 h, followed by MTT assay to evaluate cell viability.

The 7-Pathway Pattern Predicts the Response of BRAF-Mutated Melanoma Cells to BRAF/MEK Inhibitors In machine learning, support vector machines (SVMs) are a set of supervised learning models with associated learning algorithms that are primarily used in pattern recognition, classification, and regression. To test the prognostic value of the 7-pathway pattern we identified here, LIBSVM, which was developed by Chang et al (21) and is currently one of the most widely used SVM, was employed to build a classifier to predict the response of a BRAF-mutated melanoma cells to AZD6244. The pathway signatures of the 46 BRAF-mutated melanoma cell lines (Johansson dataset) were used as training set. At the initial step, all the 7 differently expressed pathways (FIG. 3B-H) were applied to build a SVM classifier. By using appropriate parameter c and γ that were obtained by the grid-search approach, the classifier achieved a predictive accuracy of 95.6% on whether the 46 melanoma cells were responsive or resistant to AZD6244 (FIG. 4A). When performed in the test set that contained 10 melanoma cell lines (GSE36133), the classifier predicted that two of the cell lines RPMI-7951 and SK-MEL-24 were highly likely to be resistant to AZD6244 (with a possibility >90%), while the other 8 cell lines were not (with a possibility <10%, except COLO829 line) (FIG. 4B). We performed cell proliferation assay in these 10 cell lines and confirmed that only RPMI-7951 and SK-MEL-24 cells had high GI50 values (>1 μM) to AZD6244 (FIG. 4B), which means that the SVM classifier achieved 100% accuracy on the test set prediction. As expected, RPMI-7951 and SK-MEL-24 cells were also resistant to BRAFV600E specific inhibitor PLX4032 (FIG. 12).

FIG. 3B-H and FIG. 4C showed that RPMI-7951 and SK-MEL-24 cells had a similar pattern in the 7 pathways as that of the AZD6244-resistant melanoma cell lines from the training set. To confirm that the 7 pathway pattern were truly present in the AZD6244-resistant cells, we detected the level of phosphor-EGFR (pEGFR), phosphor-STAT3 (pSTAT3), IκB (TNFα signaling inhibitor) and MYC by Western blot (FIG. 4D), and calculated IFN score and hypoxia score based on the expression data of several related gene (Table 3). Although the 7 pathway activities predicted by BinReg were based on the expression of numerous genes in the 10 melanoma cell lines (FIG. 4C), they overall pattern was in line with the data obtained by experimental detection of only one or several gene products, except for several data values across the 10 cell lines such as the STAT3 activity in RPMI-7951 cells (FIG. 4E).

Using the top 4, 5 or 6 pathways that have lowest randomization test p-values (FIG. 4F) to build SVM classifier also achieved the same accuracies for both training set and test set, while using less or more pathways decrease the prediction accuracy (FIG. 4G). To optimize the pathway combinations for better SVM performance, we used RFE-SVM to rank the 7 pathways (FIG. 4F) and then tested the top number of pathways respectively for SVM analysis. FIG. 4H showed that using as few as 3 pathways, including TNFα, Hypoxia and EGFR pathways, could successfully distinguish the AZD6244-resistant melanoma cell lines from the drug responsive cell lines, although it could not further increase the overall prediction accuracy.

TNFα, EGFR, IFNα and IFNγ Pathway Activities Decreased Following the Increase in the Sensitivity to AZD6244 in Two Syngenic Cell Lines.

Figure 5:
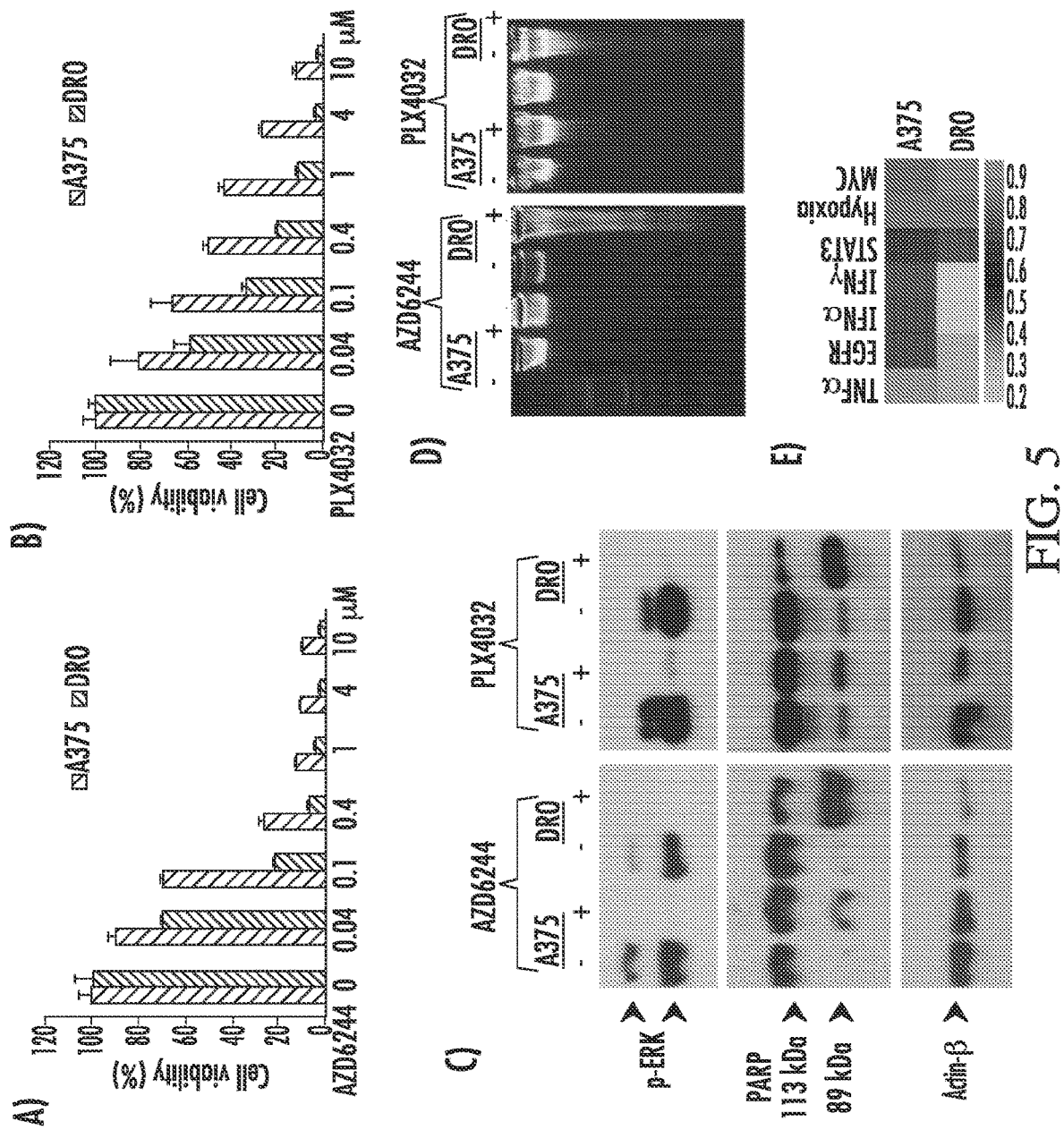
FIG. 5. DRO cell line is more sensitive to V600E BFAF/MEK inhibitors than its parent line A375 and has lower activities of TNFα, EGFR, IFNα and IFNγ pathways. MTT assay showed that DRO cell line was more sensitive than A375 cell line to AZD6244 (A) or PLX4032 (B)-induced proliferation inhibition. AZD6244 and PLX4032 induced significant cleavage of PARP (C) and DNA ladder (D) in DRO but not A375 cells. E) Activities of the 7 pathways of the 7-pathway pattern in DRO and A375 cells.

DRO cell line is a sub-line derived from A375 cells after regular passaging, which was confirmed by DNA profiling analysis using 10 STR markers (22). DRO line is much more sensitive than its parent line A375 to AZD6244 or PLX4032-induced proliferation inhibition (FIG. 5A, B). AZD6244 and PLX4032 induced significant cleavage of poly-ADP-ribose polymerase (PARP) and DNA ladder (FIG. 5C, D), representing robust apoptosis, mainly in DRO cells, but not in A375 cells.

Figure 13:
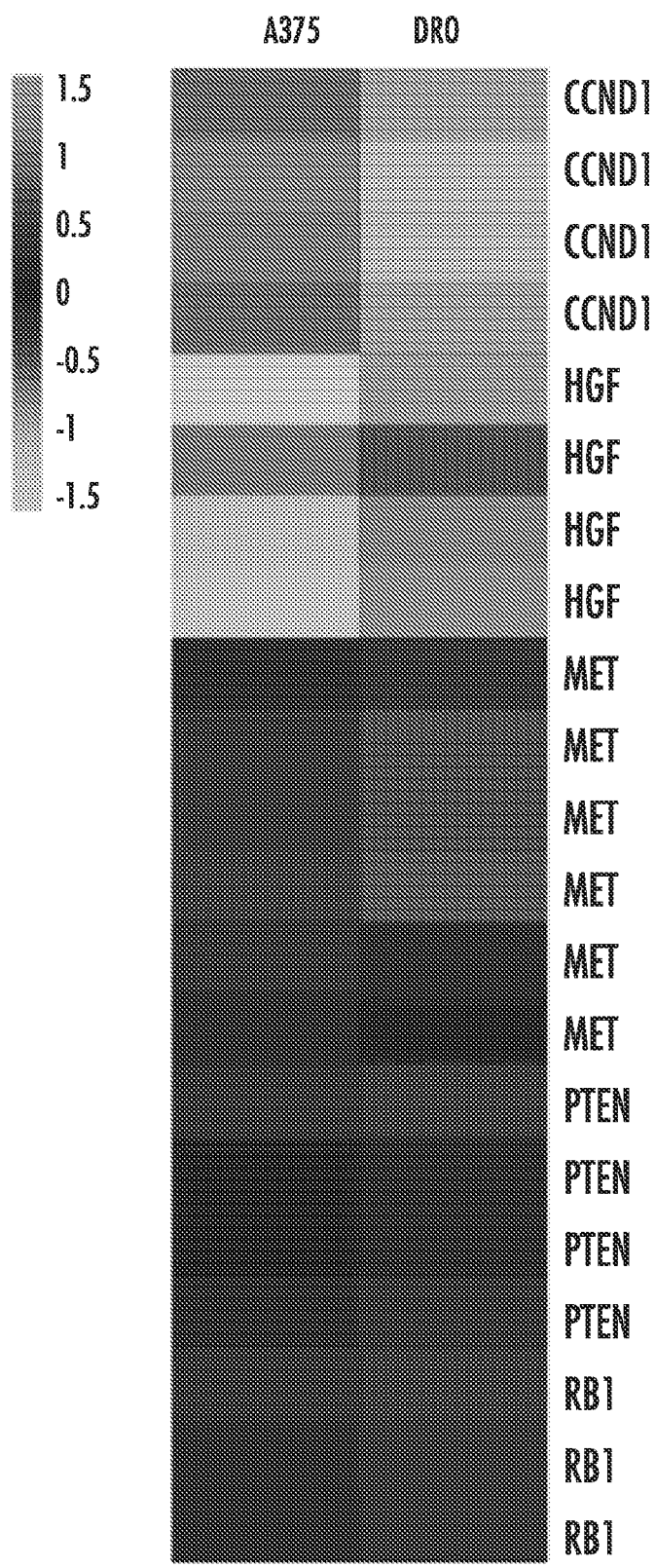
FIG. 13. The relative expression level of CCND1, HGF, MET, PTEN and RB1 in the two syngenic cell lines A375 and DRO. The gene expression data, which was extracted from cDNA microarray analysis of A375 and DRO cells as we described in Supplementary Materials and Methods, was illustrated by heatmap. Each colored cell in the heatmap represents the relative level of a gene probe in the corresponding cell line.

Except homozygous T1799A BRAF mutation and two rare homozygous CDKN2A mutations, no RAS, PTEN, PIK3CA or other types of BRAF mutations were detected in A375 and DRO cells (data not shown). In addition, genes CCND1, HGF, MET, PTEN and RB1 that might be related with the resistance of melanoma cells to BRAF/MEK inhibitors (2, 3, 5) did not show different expression levels between A375 and DRO cells, except CCND1 and HGF (FIG. 13). HGF level in DRO cells was even about 9 folds higher than that in A375 cells. Interestingly, pathway analysis based on the microarray gene expression data showed that TNFα, EGFR, IFNα and IFNγ pathway activities were much lower in DRO cells than that in A375 cells and STAT3 pathway activity was moderately lower in DRO cells (FIG. 5E), further suggesting the association between these pathways and response of BRAF-mutated melanoma cells to BRAF/MEK inhibitors.

Discussion

Correlations of Oncogenic Pathways with the Genetic Alterations in Melanoma Cells Our data showed that melanoma cells with BRAF mutations have higher activities in multiple oncogenic pathways than the cells with wild-type BRAF and RAS, including BRAF, RAS, E2F1, BCAT, IGF1, ALK and MYC signaling pathways that have been previously reported to be associated with the progression or malignant phenotype of melanoma (3, 13-16, 18, 19). This result, together with our pervious finding that mutant BRAF was associated with silence of multiple tumor-suppressor genes through epigenetic regulation (23), indicate that mutant BRAF may switch the equilibrium between the inhibitory and promoting regulation on cell renewal and proliferation to the side that favors melanoma cells acquiring higher malignant capability. This may also explain the clinical observation that melanoma patients with BRAF mutation have worse clinical features than patients with wild-type genotypes (24). It is worth noting that cells with both BRAF and PTEN alterations showed higher activities in most of the oncogenic pathways than the cells with BRAF mutation alone, which is in line with previous reports that the BRAF/MEK and PI3K pathways cooperated to promote tumor progression and enhance malignant potential of melanoma (25).

Melanoma cells with wild-type BRAF and RAS have higher activity in PR pathway than cells with BRAF or RAS mutations. Receptor Activator of Nuclear Factor κB Ligand and Inhibitor of DNA Binding 4, two major downstream effectors of PR pathway, were reported to be overexpressed in melanoma and might be involved in the metastatic spreading and development of melanoma-initiating cells (26, 27). Further studies are needed to clarify whether PR pathway is important in the pathogenesis of the melanoma without BRAF or RAS mutations.

Cross-Talks Among the Seven Pathways that were Differently Expressed Between the AZD6244-Responsive and Resistant BRAF-Mutated Melanoma Cells We found that 7 pathways showed significantly different activities between the AZD6244-responsive and resistant BRAF-mutated melanoma cells, including TNFα, EGFR, IFNα, hypoxia, IFNγ and STAT3 pathways (upregulated in AZD6244-resistant cells) and MYC pathway (downregulated in AZD6244-resistant cells). Previous studies showed that activation of EGFR and STAT3 signaling was involved in the acquired resistance of BRAF-mutated melanoma cells to BRAF/MEK inhibitors (28, 29). To our knowledge, the correlations between activities of TNFα, IFNα, hypoxia, IFNγ and MYC pathways and sensitivities of cancer cells to BRAF/MEK inhibitors, have not been reported.

Cytokines TNFα, IFNα and IFNγ are well known for their broad-spectrum anti-tumorigenic effects and have been employed for biotherapy for several cancers (30, 31). In recent years, the concept that these cytokines have pure antitumor activities has been challenged as numerous data also revealed that in certain cellular contexts the TNFα and IFN pathways could mediate tumor cell growth by promoting proliferation, survival or metastasis of cancer cells (30, 31). In addition, TNFα and IFN pathways could induce resistance to fractionated ionizing radiation and some chemotherapy drugs such as doxyrubicin and fludarabin (30-32), suggesting double-faced biological effects of these pathways.

As TNFα and IFN pathways transduce both anti- and pro-survival signaling, the final output effects of these pathways probably depend on whether the anti- and pro-survival signaling are suppressed or enhanced by other signaling pathways that crosstalk with the TNFα or IFN pathways. Studies have shown that MYC induced cellular susceptibility to the cytotoxic action of TNFα or IFNs in normal and cancer cells (33, 34), while EGF signaling could protect normal and cancer cells from TNFα or IFNs-induced cell death (35, 36). It was further demonstrated that MYC impaired TNF-induced activation of NF-kappaB transcription factor complex, while it had no effect on TNF-induced accumulation of the wild-type p53 mRNA and protein (34). Consequently, it was speculated that the activation of EGF pathway or inactivation of MYC pathway might switch the TNFα and IFN signaling from a pro-survival side to an anti-survival side. Interestingly, the TNFα or IFN pathways themselves could increase the expression or phosphorylation of EGFR while they decreased MYC expression (36-39).

Hypoxia and STAT3 pathways are also in close cross-talk with the other six pathways in the 7-pathway pattern. For example, hypoxia promoted activation of the EGFR, IFN and TNFα signaling (40-42) and degraded MYC protein in a number of cancer cells (43). On the other hand, EGF, IFNs and TNFα could increase the activity of Hypoxia-inducible factor-1 (HIF-1) in multiple cell types (44, 45). Activation of STAT3, which promotes cell proliferation, survival, angiogenesis, metastasis and is associated with a poor prognosis in many cancers, was induced by multiple potential upstream inputs including EGF, TNFα, IFNs and HIF-1 (46, 47). Conversely, activated STAT3 can induce the expression of these important molecules or increase their activities (46, 47).

Figure 6A:
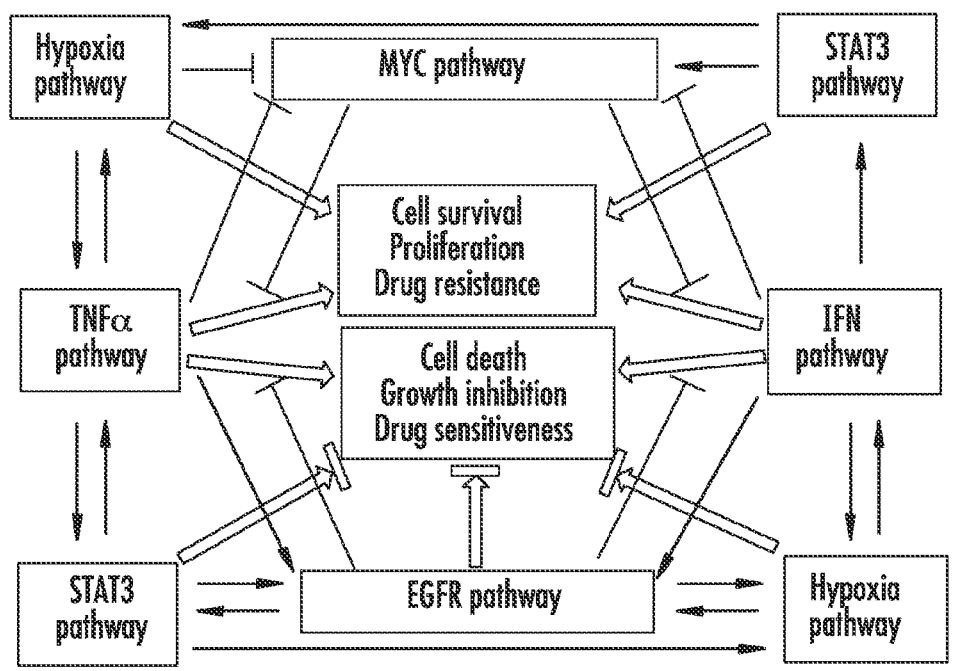
FIG. 6. Cross-talks and co-regulations among the cancer-related pathways in the 7-pathway pattern. A) Illustrations of the cross-talks among the 7 pathways. Arrows represent promotion, while flat-ended lines represent inhibition. B) and C) Pearson's correlation analysis of pathway activities based on the Johansson dataset (B) and the merged dataset (C). Heatmaps were used to depict the Pearson's correlation coefficients between any two of the 24 cancer-related pathways across the 63 (Johansson dataset) and 169 (merged dataset) melanoma samples. The red color indicates a positive correlation while blue a negative correlation. The correlation coefficients between any two of the 7 pathways in the 7-pathway pattern are highlighted with either orange (for the MYC pathway) or blue (for the other 6 pathways) boxes.
Figure 6C:
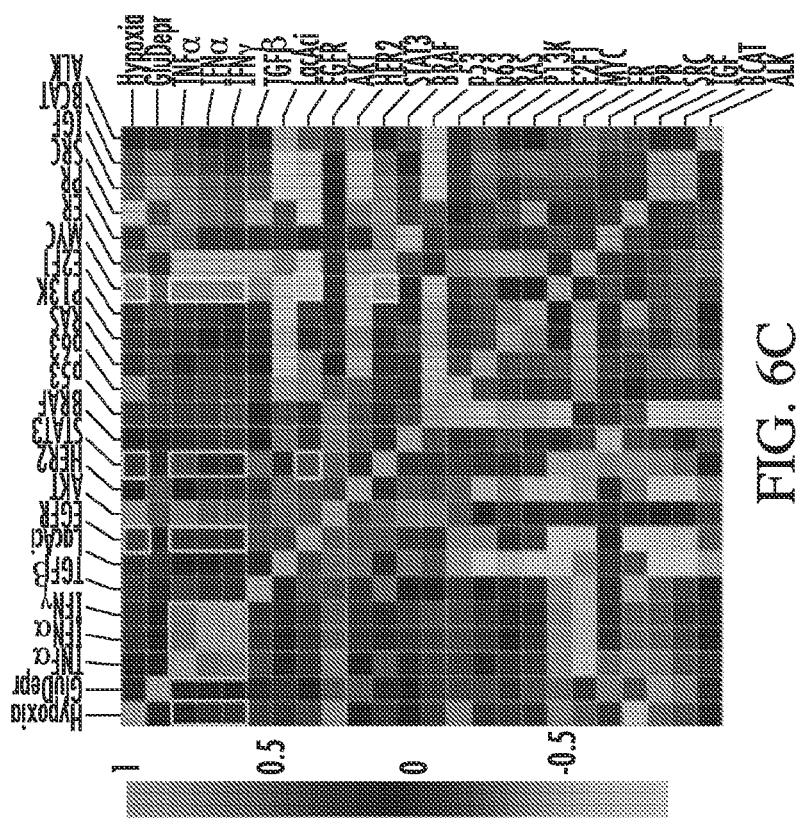
Figure 6B:
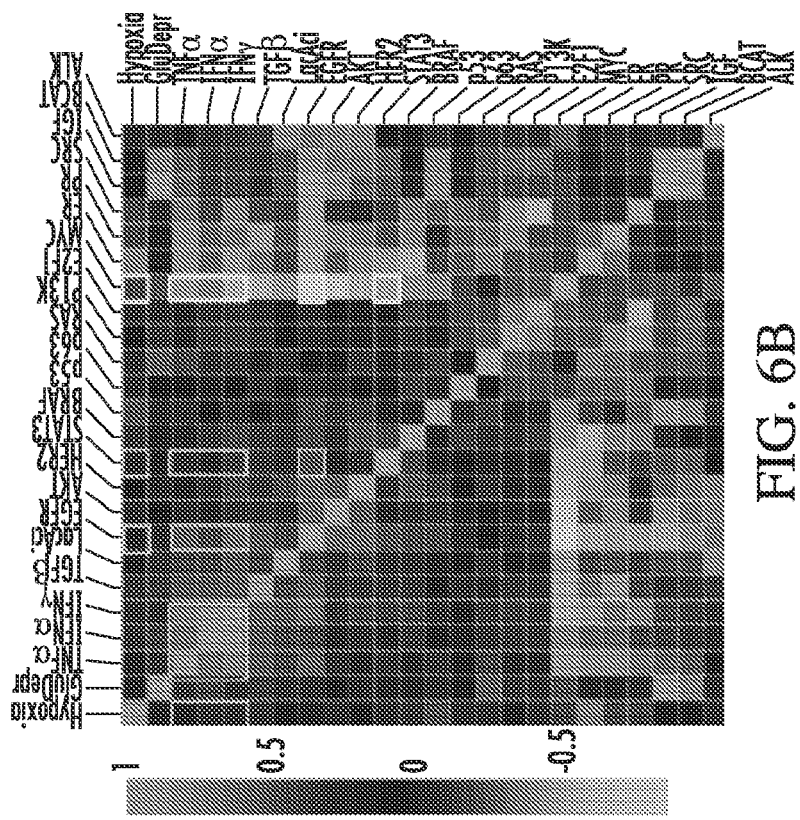

Based on the above discussion, we have summarized the close cross-talks among the 7 pathways in FIG. 6A. The co-regulation of the 7 pathways was also supported by pathway correlation analysis of the Johansson dataset and merged dataset (FIG. 6B, C). Overall, the activities of TNFα, EGFR, IFNα, hypoxia, IFNγ and STAT3 pathways were positively correlated with each other while all these 6 pathways were negatively correlated with the MYC pathway in both datasets, except that no apparent correlation was observed between hypoxia pathway and TNFα, IFNα and IFNγ in the merged dataset. This correlation indicates that melanoma cells that have activated TNFα, IFNα and IFNγ pathways incline to have high activities of EGFR, STAT3 and hypoxia pathways while they have low MYC pathway activities, which is the exact pathway pattern we observed in AZD6244-resistant BRAF-mutated melanoma cell lines. From the view point of Darwin's evolution theory, the universality of the co-regulation of the 7 pathways across the melanoma cells suggested that achieving some kind of balance through the crosstalk among these pathways might be vital for the progression of melanoma; as one type of balance, the 7-pathway pattern that exists in AZD6244-resistant melanoma cells, might favor the growth and survival of these melanoma cells and protect cells against unfavorable growth conditions, such as the AZD6244 treatment.

Association Between the 7-Pathway Pattern and the Response of Melanoma Cells to BRAF/MEK Inhibitors.

The 7-pathway pattern we identified in this study—low activity in the MYC pathway but high activities in the TNFα, EGFR, IFNα, hypoxia, IFNγ and STAT3 pathways—only exist in the AZD6244-resistant melanoma cell lines from both the training and test datasets. Moreover, in A375/DRO syngenic cell lines, the decrease of the TNFα, EGFR, IFNα, IFNγ and STAT3 pathway activities was correlated with the increase of sensitivities of cells to AZD6244/PLX4032-induced apoptosis and proliferation inhibition. These results confirmed the close association between the 7-pathway pattern and the response of melanoma cells to BRAF/MEK inhibitors.

It was recently reported that activation of EGFR pathway was involved in the development of acquired resistance of several melanoma cell lines to PLX4032 (28). Moreover, the EGFR inhibitor Lapatinib had apparently synergistic effects with PLX4032 in two PLX4032-resistant melanoma cell lines (29). These data suggested that activation of EGFR pathway alone has the potential to cause innate resistance to BRAF/MEK inhibitors in melanoma cells. However, some melanoma cell lines with high EGFR pathway activity were still sensitive to AZD6244 (FIG. 8). This suggests that the suppressing effects of EGFR signaling on the cytotoxicity of AZD6244/PLX4032 in melanoma cells might rely on certain cellular contexts. As discussed above, cross-talks among the 7 pathways are expected to suppress the pro-apoptotic effects while enhance the anti-apoptotic effects of TNFα and IFN in melanoma cells. Moreover, activation of TNFα, IFN and hypoxia pathways could cause resistance of cancer cells to chemotherapy and radiotherapy (31, 32, 48). Therefore, activation of the EGFR pathway, with the cooperation of several other pathways as indicated in the 7-pathway pattern, is more likely to cause resistance of BRAF-mutated melanoma cells to the BRAF/MEK inhibitors than EGFR pathway activation alone. Further studies to experimentally test this hypothesis may shed new light on the treatment of melanomas that are resistant to BRAF/MEK inhibitors.

Over the past decade, many multi-gene expression signatures have been demonstrated to be useful as bio-markers for risk assessment, prognostication, prediction of response to treatment, or monitoring of disease progression for various cancers. Several of these biomarkers are already in clinical application to guide treatment decisions for cancer patients (49). In the present study, the SVM classifier built with the 7-pathway pattern could predict well whether a melanoma cell will be resistant to BRAF/MEK inhibitors-. It will be interesting and important to test whether this SVM classifier can be used to predict responses of melanoma patients to BRAF/MEK inhibitors.

REFERENCE LIST (1) Lens M B, Dawes M. Global perspectives of contemporary epidemiological trends of cutaneous malignant melanoma. Br J Dermatol 2004; 150:179-85.

(2) Bollag G, Tsai J, Zhang J, Zhang C, Ibrahim P, Nolop K, et al. Vemurafenib: the first drug approved for BRAF-mutant cancer. Nat Rev Drug Discov 2012; 11:873-86.

(3) Sullivan R J, Flaherty K. MAP kinase signaling and inhibition in melanoma. Oncogene 2013; 32:2373-9.

(4) Chapman P B, Hauschild A, Robert C, Haanen J B, Ascierto P, Larkin J, et al. Improved survival with vemurafenib in melanoma with BRAF V600E mutation. N Engl J Med 2011; 364:2507-16.

(5) Fedorenko I V, Paraiso K H, Smalley K S. Acquired and intrinsic BRAF inhibitor resistance in BRAF V600E mutant melanoma. Biochem Pharmacol 2011; 82:201-9.

(6) Subramanian A, Tamayo P, Mootha V K, Mukherjee S, Ebert B L, Gillette M A, et al. Gene set enrichment analysis: a knowledge-based approach for interpreting genome-wide expression profiles. Proc Natl Acad Sci USA 2005; 102:15545-50.

(7) Bild A H, Yao G, Chang J T, Wang Q, Potti A, Chasse D, et al. Oncogenic pathway signatures in human cancers as a guide to targeted therapies. Nature 2006; %19; 439:353-7.

(8) Gatza M L, Lucas J E, Barry W T, Kim J W, Wang Q, Crawford M D, et al. A pathway-based classification of human breast cancer. Proc Natl Acad Sci USA 2010; 107: 6994-9.

(9) Freedman J A, Tyler D S, Nevins J R, Augustine C K. Use of gene expression and pathway signatures to characterize the complexity of human melanoma. Am J Pathol 2011; 178:2513-22.

(10) Gatza M L, Kung H N, Blackwell K L, Dewhirst M W, Marks J R, Chi J T. Analysis of tumor environmental response and oncogenic pathway activation identifies distinct basal and luminal features in HER2-related breast tumor subtypes. Breast Cancer Res 2011; 13:R62.

(11) West M, Ginsburg G S, Huang A T, Nevins J R. Embracing the complexity of genomic data for personalized medicine. Genome Res 2006; 16:559-66.

(12) Johansson P, Pavey S, Hayward N. Confirmation of a BRAF mutation-associated gene expression signature in melanoma. Pigment Cell Res 2007; 20:216-21.

(13) Zhuang D, Mannava S, Grachtchouk V, Tang W H, Patil S, Wawrzyniak J A, et al. C-MYC overexpression is required for continuous suppression of oncogene-induced senescence in melanoma cells. Oncogene 2008; 27:6623-34.

(14) Putzer B M, Steder M, Alla V. Predicting and preventing melanoma invasiveness: advances in clarifying E2F1 function. Expert Rev Anticancer Ther 2010; 10:1707-20.

(15) Damsky W E, Curley D P, Santhanakrishnan M, Rosenbaum L E, Platt J T, Gould Rothberg B E, et al. beta-catenin signaling controls metastasis in Braf-activated Pten-deficient melanomas. Cancer Cell 2011; 20:741-54.

(16) Satyamoorthy K, Li G, Vaidya B, Patel D, Herlyn M. Insulin-like growth factor-1 induces survival and growth of biologically early melanoma cells through both the mitogen-activated protein kinase and beta-catenin pathways. Cancer Res 2001; 61:7318-24.

(17) Li Y, Prives C. Are interactions with p63 and p73 involved in mutant p53 gain of oncogenic function? Oncogene 2007; 26:2220-5.

(18) Davies M A, Samuels Y. Analysis of the genome to personalize therapy for melanoma. Oncogene 2010; 29:5545-55.

(19) Croce C M. Oncogenes and cancer. N Engl J Med 2008; 358:502-11.

(20) Johnson W E, Li C, Rabinovic A. Adjusting batch effects in microarray expression data using empirical Bayes methods. Biostatistics 2007; 8:118-27.

(21) Chang C, Lin. L I B S V M: a library for support vector machines. ACM Transactions on Intelligent Systems and Technology 2011; 2:1-27.

(22) Schweppe R E, Klopper J P, Korch C, Pugazhenthi U, Benezra M, Knauf J A, et al. Deoxyribonucleic acid profiling analysis of 40 human thyroid cancer cell lines reveals cross-contamination resulting in cell line redundancy and misidentification. J Clin Endocrinol Metab 2008; 93:4331-41.

(23) Liu D, Liu X, Xing M. Epigenetic genes regulated by the BRAFV600E signaling are associated with alterations in the methylation and expression of tumor suppressor genes and patient survival in melanoma. Biochem Biophys Res Commun 2012; 425:45-50.

(24) Ellerhorst J A, Greene V R, Ekmekcioglu S, Warneke C L, Johnson M M, Cooke C P, et al. Clinical correlates of NRAS and BRAF mutations in primary human melanoma. Clin Cancer Res 2011; 17:229-35.

(25) Dankort D, Curley D P, Cartlidge R A, Nelson B, Karnezis A N, Damsky W E, Jr., et al. Braf(V600E) cooperates with Pten loss to induce metastatic melanoma. Nat Genet 2009; 41:544-52.

(26) Hoek K S. DNA microarray analyses of melanoma gene expression: a decade in the mines. Pigment Cell Res 2007; 20:466-84.

(27) Kupas V, Weishaupt C, Siepmann D, Kaserer M L, Eickelmann M, Metze D, et al. RANK is expressed in metastatic melanoma and highly upregulated on melanoma-initiating cells. J Invest Dermatol 2011; 131:944-55.

(28) Girotti M R, Pedersen M, Sanchez-Laorden B, Viros A, Turajlic S, Niculescu-Duvaz D, et al. Inhibiting EGF receptor or SRC family kinase signaling overcomes BRAF inhibitor resistance in melanoma. Cancer Discov 2013; 3:158-67.

(29) Held M A, Langdon C G, Platt J T, Graham-Steed T, Liu Z, Chakraborty A, et al. Genotype-selective combination therapies for melanoma identified by high-throughput drug screening. Cancer Discov 2013; 3:52-67.

(30) Bertazza L, Mocellin S. The dual role of tumor necrosis factor (TNF) in cancer biology. Curr Med Chem 2010; 17:3337-52.

(31) Khodarev N N, Roizman B, Weichselbaum R R. Molecular pathways: interferon/stat1 pathway: role in the tumor resistance to genotoxic stress and aggressive growth. Clin Cancer Res 2012; 18:3015-21.

(32) Wang L C, Okitsu C Y, Zandi E. Tumor necrosis factor alpha-dependent drug resistance to purine and pyrimidine analogues in human colon tumor cells mediated through IKK. J Biol Chem 2005; 280:7634-44.

(33) Yasuoka Y, Naomoto Y, Yamatsuji T, Takaoka M, Kimura M, Uetsuka H, et al. Combination of tumor necrosis factor alpha and interferon alpha induces apoptotic cell death through a c-myc-dependent pathway in p53 mutant H226br non-small-cell lung cancer cell line. Exp Cell Res 2001; 271:214-22.

(34) Klefstrom J, Arighi E, Littlewood T, Jaattela M, Saksela E, Evan G I, et al. Induction of TNF-sensitive cellular phenotype by c-Myc involves p53 and impaired NF-kappaB activation. EMBO J 1997; 16:7382-92.

(35) Boccellino M, Giuberti G, Quagliuolo L, Marra M, D'Alessandro A M, Fujita H, et al. Apoptosis induced by interferon-alpha and antagonized by EGF is regulated by caspase-3-mediated cleavage of gelsolin in human epidermoid cancer cells. J Cell Physiol 2004; 201:71-83.

(36) Yamaoka T, Yan F, Cao H, Hobbs S S, Dise R S, Tong W, et al. Transactivation of EGF receptor and ErbB2 protects intestinal epithelial cells from TNF-induced apoptosis. Proc Natl Acad Sci USA 2008; %19; 105:11772-7.

(37) Caraglia M, Leardi A, Corradino S, Ciardiello F, Budillon A, Guarrasi R, et al. alpha-Interferon potentiates epidermal growth factor receptor-mediated effects on human epidermoid carcinoma KB cells. Int J Cancer 1995; 61:342-7.

(38) Carlberg A L, Moberg K H, Hall D J. Tumor necrosis factor and gamma-interferon repress transcription from the c-myc P2 promoter by reducing E2F binding activity. Int J Oncol 1999; 15:121-6.

(39) Harvey W H, Harb O S, Kosak S T, Sheaffer J C, Lowe L R, Heerema N A. Interferon-alpha-2b downregulation of oncogenes H-ras, c-raf-2, c-kit, c-myc, c-myb and c-fos in ESKOL, a hairy cell leukemic line, results in temporal perturbation of signal transduction cascade. Leuk Res 1994; 18:577-85.

(40) Wang Y, Roche O, Xu C, Moriyama E H, Heir P, Chung J, et al. Hypoxia promotes ligand-independent EGF receptor signaling via hypoxia-inducible factor-mediated upregulation of caveolin-1. Proc Natl Acad Sci USA 2012; 109:4892-7.

(41) Terui K, Haga S, Enosawa S, Ohnuma N, Ozaki M. Hypoxia/re-oxygenation-induced, redox-dependent activation of STAT1 (signal transducer and activator of transcription 1) confers resistance to apoptotic cell death via hsp70 induction. Biochem J 2004; 380:203-9.

(42) Yu X, Deng L, Wang D, Li N, Chen X, Cheng X, et al. Mechanism of TNF-alpha autocrine effects in hypoxic cardiomyocytes: initiated by hypoxia inducible factor 1alpha, presented by exosomes. J Mol Cell Cardiol 2012; 53:848-57.

(43) Li Q, Kluz T, Sun H, Costa M. Mechanisms of c-myc degradation by nickel compounds and hypoxia. PLoS One 2009; 4:e8531.

(44) Gerber S A, Pober J S. IFN-alpha induces transcription of hypoxia-inducible factor-1alpha to inhibit proliferation of human endothelial cells. J Immunol 2008; 181:1052-62.

(45) Hellwig-Burgel T, Stiehl D P, Wagner A E, Metzen E, Jelkmann W. Review: hypoxia-inducible factor-1 (HIF-1): a novel transcription factor in immune reactions. J Interferon Cytokine Res 2005; 25:297-310.

(46) Johnston P A, Grandis J R. STAT3 signaling: anti-cancer strategies and challenges. Mol Intery 2011; 11:18-26.

(47) Grivennikov S I, Karin M. Dangerous liaisons: STAT3 and NF-kappaB collaboration and crosstalk in cancer. Cytokine Growth Factor Rev 2010; 21:11-9.

(48) Mamlouk S, Wielockx B. Hypoxia-inducible factors as key regulators of tumor inflammation. Int J Cancer 2013; 132:2721-9.

(49) Majewski I J, Bernards R. Taming the dragon: genomic biomarkers to individualize the treatment of cancer. Nat Med 2011; 17:304-12.

(50) Dry J R, Pavey S, Pratilas C A, Harbron C, Runswick S, Hodgson D, et al. Transcriptional pathway signatures predict MEK addiction and response to selumetinib (AZD6244). Cancer Res 2010; 70:2264-73.

Supplementary Materials and Methods

Generation of Signatures for BRAF, ALK and IGF1 Pathways.

RMA normalized data was used for the signature generation and activity prediction for BRAF, ALK and IGF1 pathways. To generate the BRAF pathway signature, the gene expression data (GSE20051) (3) of the 5 BRAFV600E melanoma cell lines treated with or without BRAFV600E inhibitor PLX4032 (250 nM) was used as training set. The gene expression data of the 7 BRAFV600E cancer lines treated with or without MEK inhibitor PD0325901 (GSE10086) (4), the BRAFV600E melanoma cell line A375 with Doxycycline (Dox)-inducible BRAF knock-down (GSE13487) (5), and the melanocyte with forced expression of BRAFV600E (GSE13827), were used to as test sets to validate the BRAF pathway signature. For generation of IGF1 pathway signature, the gene expression data of human neuroblastoma cell line SK-N-AS treated with or without anti-IGF1R antibody (GSE11959) (6) was used as training set, and the expression data of breast cancer cell line MCF7 treated with or without IGF1 (GSE26834) (7) was used to validate the signature. For ALK pathway, the gene expression data of anaplastic large cell lymphoma cell line TS treated with or without ALK inhibitors A2 or A3 (GSE6184) (8) was used to generate signature, which was then validated by the gene expression data of TS cells with or without knock-down of ALK (GSE6184) (8), and by dataset GSE25118 (9) in which xenograft tumors formed by lung cancer cell line NCI-H2228 were treated with ALK inhibitor CH5424802. The signature conditions for the 3 pathways were detailed in Table 4.

Figure 14:
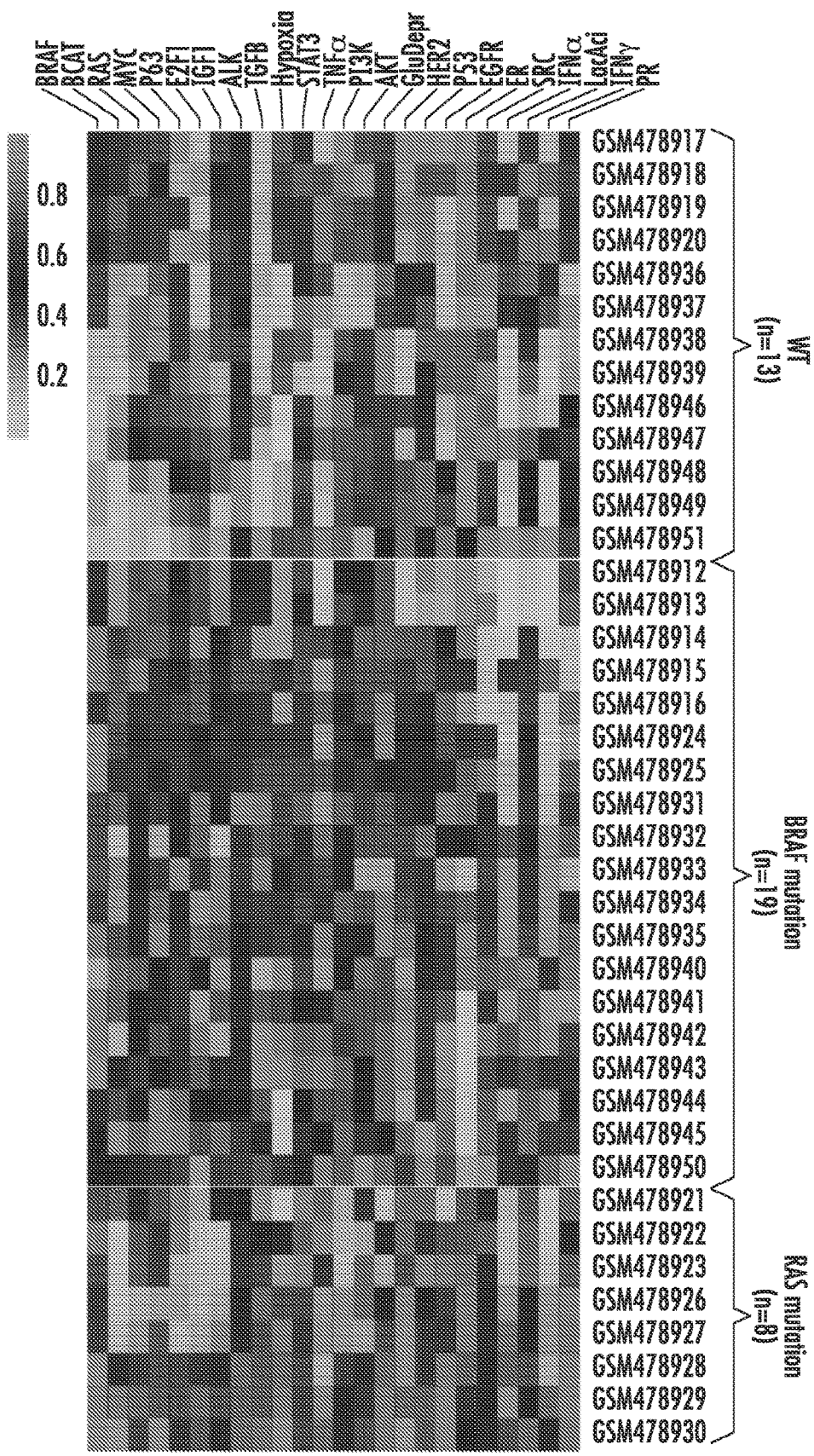
FIG. 14. Heatmap of cancer-related pathway activities in melanoma cells with different genetic alterations (dataset GSE19293). Each colored cell in the heatmap represents the predicted possibility of one pathway in the corresponding cell line. The 40 of the 52 melanoma samples that have information available on BRAF and RAS mutations were classified into 3 groups according to their genotypes in these two oncogenes. The sample names listed at the right side of heatmap are accession numbers of these samples in GEO database. The two white lines separate the heatmap into three parts that correspond to the 3 groups of samples respectively. We observed similar oncogenic pathways were activated in BRAF-mutated melanoma cells in this dataset as those in Johansson and merged datasets (FIGS. 8 and 4). However, we did not include this dataset into the merged dataset because the melanoma samples of this dataset were from the patients treated with melphalan.

Generation of Merged Dataset for Validation of Mutant BRAF-Associated Pathways in Melanoma Five melanoma datasets, including GSE10282(10), GSE10916 (11), GSE15605 (12), GSE22787 (13) and GSE33728 (14), were normalized by RNA and MAS5.0 approaches respectively. The gene expression data of the 5 datasets normalized by the same approach were then merged using ComBat program (15) to remove dataset-specific biases. Principal component analysis was used to check whether the dataset-specific biases were successfully removed. Among 196 samples of the 5 datasets, 2 samples harbor both BRAF and RAS mutations, and 24 samples are from normal tissues. These 26 samples were excluded from the merged dataset, and the remaining 169 melanoma samples that have confirmed BRAF and RAS mutation information, were used for validation of mutant BRAF-associated cancer-related pathways. Although when analyzing melanoma dataset GSE19293, we found activation of the similar oncogenic pathways were associated with BRAF mutation as we observed in Johansson dataset (FIG. 14), we did not include this dataset into the merged dataset because the melanoma samples of this dataset were from the patients treated with melphalan. We also did not include the melanoma dataset GSE4845 (16) since only MAS5.0 normalized gene expression data but not the raw array data was available in the GEO database.

Cell Proliferation Assay

Cells (800-1200/well) were seeded into 96-well plates and cultured with different concentration of MEK inhibitor AZD6244 (Selleck Chemicals, Houston, Tex.) or BRAFV600E inhibitor PLX4032 (Plexxikon Inc., Berkeley, Calif.). After 72 h treatments, cell culture was added with 10 µl of 5 mg/ml MTT agent (3-(4,5-Dimethylthiazol-2-yl)-2, 5-diphenyltetrazolium bromide, Sigma St. Louis, Mo.) and incubated for 4 h, followed by addition of 100 µl of 10% SDS solution and a further incubation overnight. The plates were then read on a microplate reader using the test wavelength of 570 nm and the reference wavelength of 670 nm. Five duplicates were done to determine each data point. GI50 was calculated as previously reported (21).

RNA Extraction and Real-Time Quantitative RT-PCR (qRT-PCR) Analysis

Total RNA was isolated using RNeasy plus kit (Qiagen), following by reverse-transcription using SuperScript First-Strand Synthesis kit (Invitrogen). SYBR Green based real-time qRT-PCR analysis was carried out in an ABI Prism 7900HT Sequence Detector (Applied Biosystems). The expression value of each gene was normalized to GAPDH to determine the relative level of RNA in each sample using the $2^{-\Delta\Delta Ct}$ method. The primers used in this study were listed in Table 5.

Calculation of Interferon (IFN) Score and Hypoxia Score

IFN score was calculated based on the average gene expression value for IFN—inducible genes IF16, IFIT3 and STAT1 according to the Assassi's method (22) with some modification. Briefly, The means and standard deviations (SD) of the respective genes were calculated across the 10 melanoma cell lines of the test dataset. The respective averages were then subtracted from the expression values in each cell line and the residues were divided by the SD value for the same gene in order to calculate the relative number of SDs above average level of the cell lines. This number was generated for each of the 3 genes and then summed to yield the final score. The hypoxia score was calculated using the formula reported previously (23): Hypoxia Score=mean (expression ratio UP regulated genes in Log base2)—mean (expression ratio Down regulated genes in Log base2), where UP regulated genes include CCNG2, WDR45L, ERO1L and EGLN3, DOWN regulated genes include MAT1A, RCL1, and FGF21, and the expression ratio is calculated through dividing the expression level of one gene in an individual cell line by the average level of the same gene across the 10 melanoma cell lines. Expression levels of all the above genes were examined by real-time qRT-PCR.

Western Blotting Analysis

Cells were lysed in the RIPA buffer supplemented with phosphatase and protease inhibitors (Sigma, MO) and protein blot analyses were performed as we previously described (24). The antibody against IκB (#9242), PARP (#9542), phospho-EGFR (#3777), phospho-STAT3 (#9145) were from Cell Signaling (Boston, Mass.). The other antibodies used in the present study, including anti-phospho-ERK (Sc-7383), anti MYC (sc-47694) and anti-actin (Sc-1616-R), were purchased from Santa Cruz (Santa Cruz, Calif.).

Microarray Procedure and Data Processing

Total RNA was amplified using 3' IVT Express Kit (Affymetrix) according to manufatural protocol. Biotinylated cRNA was fragmented and hybridized to the Affymetrix GeneChip human PrimeView™ arrays. After hybridization, arrays were washed and stained. Fluorescence was then detected using the Affymetrix 3000 GeneArray Scanner. Prior to pathway activity prediction by BinReg, the probeset ID in PrimeView™ array were converted into the corresponding probeset ID in HG-U133 plus 2.0 array using HG-U219 to HG-U133_Plus_2 Best match table (http://www.affymetrix.com/support/).

TABLE 1

Pathways differently expressed between the WT and BRAF-mutated cells in the Johansson and merged datasets.

| Gene expression | p-value for the pathway activity difference ( WT vs. BRAF-mutated melanoma) [‡] | | | | | | | | |
|---|---|---|---|---|---|---|---|---|---|
| Dataset | BRAF | RAS | E2F1 | BCAT | IGF | ALK | PR | MYC | p63 |
| Johansson dataset [*] | 0.019 | 0.011 | 0.025 | 0.008 | 0.008 | 0.004 | 0.008 | 0.036 | 0.082 |
| Merged dataset [†] | <0.001 | <0.001 | 0.062 | 0.002 | 0.119 | 0.010 | 0.011 | 0.015 | <0.001 |

[*] We combined the BRAF and B&P groups in the Johansson dataset into one group and calculated the p-values for the differently expressed pathways between the combined group (n = 37) and the WT group (n = 7).
[†] For the merged dataset, we calculated the p-values for the differently expressed pathways between the melanoma samples carrying BRAF mutation alone (n = 80) and the WT (wild-type in both BRAF and RAS) group (n = 59).
[‡] The BRAF, RAS, E2F1, BCAT IGF1, ALK, p63 and MYC pathways were upregulated in BRAF-mutated cells while the PR pathway was upregulated in WT cells in both datasets. $P \leq 0.025$ was set as statistical significance (randomization test).

TABLE 2

List of microarray datasets used in this study

| Accession number | Affymetrix chip | Sample derived from | Normalization method | Reference | Purpose |
|---|---|---|---|---|---|
| GSE20051 | U133A 2.0 | melanoma | RMA | (3) | Generation BRAF pathway signature |
| GSE10086 | U133A 2.0 | melanoma | RMA | (4) | |
| GSE13487 | U133 Plus 2.0 | melanoma | RMA | (5) | |
| GSE13827 | U133 Plus 2.0 | melanocyte | RMA | | |
| GSE11959 | U133 Plus 2.0 | neuroblastoma | RMA | (6) | Generation IGF1 pathway signature |
| GSE26834 | U133A 2.0 | breast cancer | RMA | (7) | |
| GSE6184 | U133A | lymphoma | RMA | (8) | Generation ALK pathway signature |
| GSE25118 | U133 Plus 2.0 | lung cancer | RMA | (9) | |
| GSE7127 | U133 Plus 2.0 | melanoma | RMA, MAS5.0 | (18) | Analysis of cancer-related pathways in melanoma cells |
| GSE36133 | U133 Plus 2.0 | melanoma | RMA, MAS5.0 | (19) | |
| GSE10282 | U133 Plus 2.0 | melanoma | RMA, MAS5.0 | (10) | |
| GSE10916 | U133 Plus 2.0 | melanoma | RMA, MAS5.0 | (11) | |
| GSE15605 | U133 Plus 2.0 | melanoma | RMA, MAS5.0 | (12) | |
| GSE22787 | U133A 2.0 | melanoma | RMA, MAS5.0 | (13) | |
| GSE33728 | U133 Plus 2.0 | melanoma | RMA, MAS5.0 | (14) | |
| GSE19293 | U133 Plus 2.0 | melanoma | RMA, MAS5.0 | (10) | |

TABLE 3

IFN and hypoxia score and related gene expression level in melanoma cell lines of test set

| Cell line | Relative gene expression level | | | | | |
|---|---|---|---|---|---|---|
| | IFI6 | IFIT | STAT1 | CCNG2 | EGLN3 | ERO1 |
| Malme-3M | 2.40759 | 1.648191 | 2.487097 | 0.848997 | 2.295199 | 1.975493 |
| UACC62 | 1.067513 | 0.536834 | 0.363559 | 0.213631 | 2.572084 | 1.133719 |
| COL0829 | 4.021983 | 2.127985 | 3.859976 | 2.14561 | 4.000959 | 1.713998 |
| A375 | 1 | 1 | 1 | 1 | 1 | 1 |
| SK-MEL-1 | 0.957326 | 0.999992 | 1.51324 | 0.971803 | 5.907743 | 0.727072 |
| SK-MEL-28 | 3.200604 | 1.095467 | 1.064792 | 0.613747 | 7.419518 | 1.602241 |
| SK-MEL-5 | 4.314497 | 0.763784 | 2.056336 | 0.359855 | 7.9371 | 2.299816 |
| SK-MEL-3 | 9.216813 | 1.342466 | 2.312867 | 0.626663 | 4.468678 | 0.927341 |
| SK-MEL-24 | 3.758311 | 2.218207 | 2.789336 | 0.790282 | 3.8276 | 1.354469 |
| RPMI7951 | 6.367626 | 2.527684 | 4.759736 | 2.270225 | 19.08355 | 3.460486 |

| Cell line | Relative gene expression level | | | IFN score | hypoxia score |
|---|---|---|---|---|---|
| | MAT1A | RCL1 | WDR45 | | |
| Malme-3M | 6.637132 | 0.514833 | 1.132945 | 0.059629 | −1.26477 |
| UACC62 | 0.123009 | 0.332073 | 0.824776 | −3.67664 | 1.157019 |
| COL0829 | 0.99606 | 0.411735 | 0.769122 | 2.406933 | 0.608457 |
| A375 | 1 | 1 | 1 | −2.54318 | −0.90959 |
| SK-MEL-1 | 2.912717 | 0.228218 | 0.668817 | −2.17858 | −0.24472 |
| SK-MEL-28 | 0.121381 | 0.260269 | 1.101889 | −1.5127 | 2.334342 |
| SK-MEL-5 | 5.525425 | 0.623215 | 0.885534 | −0.84313 | −1.16648 |

TABLE 3-continued

IFN and hypoxia score and related gene expression level in melanoma cell lines of test set

| | | | | | |
|---|---|---|---|---|---|
| SK-MEL-3 | 3.463824 | 0.514315 | 3.953395 | 2.078559 | −0.48617 |
| SK-MEL-24 | 0.749189 | 0.116093 | 0.890621 | 1.645401 | 1.318902 |
| RPMI7951 | 0.40563 | 0.32029 | 0.768833 | 4.56371 | 2.274768 |

* We did not include the expression data of FGF1 as no expression of this gene was detected in the 10 melanoma cells

TABLE 4

Signature conditions for prediction of BRAF, ALK and IGF1 pathway activities

| | BRAF pathway | | | IGF pathway | | | ALK pathway | | |
|---|---|---|---|---|---|---|---|---|---|
| Pathway | Intercept | Probeset | Coefficient | Intercept | Probeset | Coefficient | Intercept | Probeset | Coefficient |
| Signature parameters, probes, and regression weights | 14.3885 | 204011 at | 0.071933 | 16.955 | 203967 at | 0.118417 | 10.0664 | 202431 s at | 0.041195 |
| | | 221489 s at | 0.065591 | | 219493 at | 0.103027 | | 201008 s at | −0.03269 |
| | | 208892 s at | 0.061571 | | 208368 s at | 0.101238 | | 201009 s at | −0.03207 |
| | | 204420 at | 0.0581 | | 220651 s at | 0.097925 | | 201010 s at | −0.02891 |
| | | 208891 at | 0.05752 | | 201890 at | 0.097249 | | 205476 at | 0.028608 |
| | | 201631 s at | 0.054375 | | 203968 s at | 0.08998 | | 204456 s at | 0.027823 |
| | | 203349 s at | 0.046774 | | 219512 at | 0.071284 | | 208892 s at | 0.027673 |
| | | 203320 at | 0.04529 | | 201202 at | 0.070657 | | 208891 at | 0.027401 |
| | | 203348 s at | 0.045046 | | 218585 s at | 0.055784 | | 212942 s at | 0.027313 |
| | | 208712 at | 0.043706 | | 222036 s at | 0.054354 | | 207433 at | 0.026895 |
| | | 201694 s at | 0.041637 | | 218564 at | 0.054294 | | 206729 at | 0.025125 |
| | | 208893 s at | 0.040661 | | 215071 s at | −0.05347 | | 204908 s at | 0.024896 |
| | | 204014 at | 0.040439 | | 219961 s at | −0.05111 | | 209933 s at | 0.023764 |
| | | 204401 at | 0.040081 | | 201286 at | 0.049968 | | 205681 at | 0.022932 |
| | | 216375 s at | 0.039219 | | 209102 s at | −0.0488 | | 203023 at | 0.022354 |
| | | 206233 at | 0.037051 | | 202589 at | 0.048715 | | 219386 s at | 0.022154 |
| | | 221911 at | 0.036634 | | 2028 s at | 0.048669 | | 204457 s at | 0.021802 |
| | | 201920 at | 0.035995 | | 206102 at | 0.04609 | | 214617 at | 0.02173 |
| | | 203607 at | 0.035173 | | 204825 at | 0.045819 | | 202499 s at | 0.021125 |
| | | 204015 s at | 0.03459 | | 219306 s at | 0.045388 | | 214011 s at | 0.020582 |
| | | 222088 s at | 0.032234 | | 213906 at | 0.0452 | | 219911 s at | 0.020071 |
| | | 202498 s at | 0.032225 | | 221582 at | −0.04406 | | 210845 s at | 0.019438 |
| | | 202081 at | 0.031943 | | 222037 at | 0.042962 | | 36711 at | 0.018887 |
| | | 202693 s at | 0.030673 | | 202105 at | −0.04144 | | 210439 at | 0.01882 |
| | | 212558 at | 0.026245 | | 204768 s at | 0.040961 | | 209325 s at | 0.018422 |
| | | 204973 at | 0.024471 | | 204244 s at | 0.038371 | | 211559 s at | −0.01802 |
| | | 214613 at | 0.021575 | | 207170 s at | −0.03817 | | 206341 at | 0.01786 |
| | | 219168 s at | 0.021356 | | 211767 at | 0.037423 | | 201963 at | 0.017774 |
| | | 210174 at | −0.02124 | | 210766 s at | 0.037354 | | 203119 at | 0.017086 |
| | | 217053 x at | 0.021221 | | 201710 at | 0.036981 | | 207072 at | 0.01705 |
| | | 201328 at | 0.020347 | | 202338 at | 0.036686 | | 203622 s at | 0.016969 |
| | | 202770 s at | −0.01993 | | 203432 at | 0.036592 | | 219714 s at | 0.016785 |
| | | 218247 s at | 0.019915 | | 201384 s at | −0.03622 | | 201700 at | 0.01667 |
| | | 202769 at | −0.01979 | | 216237 s at | 0.036145 | | 217738 at | 0.016006 |
| | | 206501 x at | 0.019476 | | 219555 s at | 0.035273 | | 203233 at | 0.0159 |
| | | 211603 s at | 0.019386 | | 217905 at | 0.035272 | | 217739 s at | 0.015678 |
| | | 221752 at | 0.019149 | | 202580 x at | 0.03507 | | 209684 at | −0.0156 |
| | | 204695 at | 0.018634 | | 202431 s at | −0.03489 | | 202081 at | 0.01557 |
| | | 201904 s at | 0.018141 | | 204947 at | 0.034484 | | 207275 s at | 0.015339 |
| | | 218513 at | 0.017612 | | 203661 s at | −0.03404 | | 201489 at | 0.015254 |
| | | 207667 s at | 0.01736 | | 218350 s at | 0.032833 | | 203304 at | −0.01514 |
| | | 203967 at | 0.017216 | | 202503 s at | 0.032705 | | 213524 s at | 0.014917 |
| | | 219031 s at | 0.017157 | | 212141 at | 0.032035 | | 202068 s at | 0.014884 |
| | | 217061 s at | 0.017084 | | 213113 s at | 0.031794 | | 201675 at | 0.014738 |
| | | 56256 at | −0.0164 | | 202726 at | 0.031751 | | 208152 s at | 0.014363 |
| | | 211686 s at | 0.016129 | | 205339 at | 0.031547 | | 212646 at | 0.014351 |
| | | 214427 at | 0.0161 | | 204531 s at | 0.030423 | | 209765 at | 0.014331 |
| | | 213793 s at | 0.015489 | | 201700 at | 0.030187 | | 203821 at | 0.014251 |
| | | 209317 at | 0.014986 | | 213008 at | 0.030133 | | 213189 at | 0.014149 |
| | | 203612 at | 0.01478 | | 201637 s at | −0.03003 | | 217122 s at | −0.01385 |
| | | 202971 s at | 0.014761 | | 201930 at | 0.02969 | | 207270 x at | 0.013711 |
| | | 212272 at | −0.01459 | | 209866 s at | 0.029164 | | 207075 at | 0.013654 |
| | | 220651 s at | 0.014569 | | 219556 at | 0.028989 | | 211372 s at | 0.01355 |
| | | 203480 s at | 0.014548 | | 201584 s at | 0.028904 | | 202638 s at | 0.01349 |
| | | 202378 s at | 0.014185 | | 203856 at | 0.028891 | | 201490 s at | 0.013268 |
| | | 221910 at | 0.013896 | | 214426 x at | 0.028637 | | 205227 at | 0.013221 |
| | | 201197 at | 0.013699 | | 219148 at | 0.028491 | | 218331 s at | 0.01267 |
| | | 208659 at | 0.012692 | | 211851 x at | 0.027999 | | 202688 at | 0.012481 |
| | | 218156 s at | 0.012549 | | 207761 s at | −0.02798 | | 212434 at | 0.012435 |
| | | 218769 s at | −0.01248 | | 203976 s at | 0.026007 | | 219248 at | 0.012139 |
| | | 204568 at | −0.01141 | | 213951 s at | 0.024305 | | 217853 at | 0.011883 |
| | | 218590 at | 0.011378 | | 218976 at | −0.02389 | | 213198 at | 0.011804 |

TABLE 4-continued

Signature conditions for prediction of BRAF, ALK and IGF1 pathway activities

| Pathway | BRAF pathway | | IGF pathway | | ALK pathway | |
|---|---|---|---|---|---|---|
| | Intercept Probeset | Coefficient | Intercept Probeset | Coefficient | Intercept Probeset | Coefficient |
| | 221931 s at | 0.011247 | 202715 at | 0.023792 | 211269 s at | 0.011793 |
| | 203968 s at | 0.010932 | 216026 s at | 0.023664 | 202613 at | 0.011771 |
| | 213900 at | −0.01088 | 212597 s at | 0.023198 | 218016 s at | 0.01176 |
| | 207515 s at | 0.01065 | 206593 s at | 0.022928 | 219099 at | 0.01166 |
| | 204696 s at | 0.010236 | 216041 x at | −0.02272 | 203201 at | 0.011603 |
| | 218239 s at | 0.010213 | 217990 at | −0.02247 | 218708 at | 0.011575 |
| | 205198 s at | −0.01018 | 204178 s at | 0.021241 | 203234 at | 0.011496 |
| | 221868 at | −0.00978 | 219042 at | 0.021068 | 202478 at | 0.011388 |
| | 221688 s at | 0.009694 | 213379 at | 0.020304 | 219394 at | 0.011255 |
| | 209271 at | −0.00966 | 208717 at | −0.02005 | 203574 at | 0.011251 |
| | 218048 at | −0.00933 | 201970 s at | 0.019322 | 218512 at | 0.011048 |
| | 203733 at | −0.00933 | 203456 at | −0.0182 | 218732 at | 0.01085 |
| | 212346 s at | −0.00927 | 202623 at | −0.0176 | 201479 at | 0.010573 |
| | 218431 at | −0.00901 | 201922 at | −0.01705 | 214427 at | 0.010568 |
| | 209482 at | 0.008365 | 210826 s at | −0.01548 | 214438 at | 0.010522 |
| | 202522 at | 0.008245 | 221476 s at | −0.01529 | 205895 s at | 0.010431 |
| | 217650 x at | 0.00812 | 201682 at | −0.01493 | 202138 x at | 0.010234 |
| | 212719 at | −0.008 | 212247 at | 0.014883 | 200875 s at | 0.010232 |
| | 219361 s at | 0.007525 | 208905 at | 0.014107 | 202878 s at | 0.010212 |
| | 202248 at | 0.007403 | 205061 s at | 0.013931 | 218866 s at | 0.00991 |
| | 203094 at | 0.00707 | 201007 at | −0.01362 | 209433 s at | 0.009774 |
| | 201144 s at | 0.006818 | 217946 s at | 0.013122 | 212766 s at | 0.009705 |
| | 212216 at | −0.00596 | 213893 x at | −0.01234 | 205882 x at | −0.0097 |
| | 200754 x at | 0.005815 | 214699 x at | −0.01225 | 208433 s at | 0.009479 |
| | 203871 at | 0.005676 | 212048 s at | 0.012003 | 218501 at | 0.008404 |
| | 201700 at | 0.005658 | 221906 at | 0.011681 | 212770 at | 0.008114 |
| | 214330 at | 0.00559 | 212639 x at | 0.011453 | 204028 s at | −0.0077 |
| | 215113 s at | 0.005545 | 202522 at | −0.01068 | 205039 s at | 0.007635 |
| | 207648 at | −0.00499 | 210027 s at | −0.0091 | 204905 s at | 0.007538 |
| | 211569 s at | −0.00477 | 209440 at | 0.008197 | 202201 at | −0.00743 |
| | 205982 x at | −0.00424 | 201815 s at | −0.00769 | 208815 x at | 0.007349 |
| | 218920 at | −0.00388 | 204030 s at | −0.00765 | 209514 s at | 0.007283 |
| | 217962 at | 0.003695 | 212691 at | 0.006792 | 210951 x at | 0.006544 |
| | 219548 at | −0.00356 | 209210 s at | −0.00581 | 209122 at | −0.00635 |
| | 215784 at | 0.003092 | 202658 at | −0.0057 | 218497 s at | 0.00609 |
| | 217670 at | 0.003063 | 218418 s at | 0.005452 | 219123 at | 0.005243 |
| | 206158 s at | 0.003007 | 202475 at | 0.005226 | 215091 s at | 0.004938 |
| | 201223 s at | 0.0026 | 205036 at | 0.003886 | 203893 at | 0.004557 |

TABLE 5 qRT-PCR Primers used for the analysis of IFN and hypoxia score

| primer name | Primer Sequence | | Product size |
|---|---|---|---|
| IFI6 | GGTCTGCGATCCTGA ATGGG (SEQ ID NO: 1) | TCACTATCGAGATAC TTGTGGGT (SEQ ID NO: 2) | 145 |
| IFIT3 | AGAACAAATCAGCCT GGTCA (SEQ ID NO: 3) | CCTTGAGACACTGTC TTCCT (SEQ ID NO: 4) | 152 |
| STAT1 | CTGCTCCTTTGGTTG AATCC (SEQ ID NO: 5) | GCTGAAGTTCGTACC ACTGAGA (SEQ ID NO: 6) | 75 |
| CCNG2 | TCTGTATTAGCCTTG TGCCTTCT (SEQ ID NO: 7) | CCTTGAAACGATCCA AACCAAC (SEQ ID NO: 8) | 213 |
| WDR45L | CTCCTGCCGTGTAAC CCTC (SEQ ID NO: 9) | CCCAGATCATTACTT TGTTGGGA (SEQ ID NO: 10) | 250 |
| ERO1L | GCCAGGTTAGTGGTT ACTTGG (SEQ ID NO: 11) | GGCCTCTTCAGGTTT ACCTTGT (SEQ ID NO: 12) | 142 |
| EGLN3 | CTGGGCAAATACTAC GTCAAGG (SEQ ID NO: 13) | GACCATCACCGTTGG GGTT (SEQ ID NO: 14) | 106 |
| MAT1A | TCATGTTCACATCGG AGTCTGT (SEQ ID NO: 15) | CATGCCGGTCTTGCA CACT (SEQ ID NO: 16) | 140 |
| RCL1 | AAGGCAACAGCACTC CCTTT (SEQ ID NO: 17) | CCCGTCGCACAATCT TCAGTT (SEQ ID NO: 18) | 76 |
| FGF21 | GCCTTGAAGCCGGGA GTTATT (SEQ ID NO: 19) | GTGGAGCGATCCATA CAGGG (SEQ ID NO: 20) | 93 |

REFERENCE LIST FOR SUPPLEMENTARY MATERIALS AND METHODS (1) Gatza M L, Lucas J E, Barry W T, Kim J W, Wang Q, Crawford M D, et al. A pathway-based classification of human breast cancer. Proc Natl Acad Sci USA 2010; 107: 6994-9.

(2) Gatza M L, Kung H N, Blackwell K L, Dewhirst M W, Marks J R, Chi J T. Analysis of tumor environmental response and oncogenic pathway activation identifies distinct basal and luminal features in HER2-related breast tumor subtypes. Breast Cancer Res 2011; 13:R62.

(3) Joseph E W, Pratilas C A, Poulikakos P I, Tadi M, Wang W, Taylor B S, et al. The RAF inhibitor PLX4032 inhibits ERK signaling and tumor cell proliferation in a V600E BRAF-selective manner. Proc Natl Acad Sci USA 2010; 107:14903-8.

(4) Pratilas C A, Taylor B S, Ye Q, Viale A, Sander C, Solit D B, et al. (V600E)BRAF is associated with disabled feedback inhibition of RAF-MEK signaling and elevated transcriptional output of the pathway. Proc Natl Acad Sci USA 2009; 106:4519-24.

(5) Hoeflich K P, Herter S, Tien J, Wong L, Berry L, Chan J, et al. Antitumor efficacy of the novel RAF inhibitor GDC-0879 is predicted by BRAFV600E mutational status and sustained extracellular signal-regulated kinase/mitogen-activated protein kinase pathway suppression. Cancer Res 2009; 69:3042-51.

(6) Shang Y, Mao Y, Batson J, Scales S J, Phillips G, Lackner M R, et al. Antixenograft tumor activity of a humanized anti-insulin-like growth factor-I receptor monoclonal antibody is associated with decreased AKT activation and glucose uptake. Mol Cancer Ther 2008; 7:2599-608.

(7) Casa A J, Potter A S, Malik S, Lazard Z, Kuiatse I, Kim H T, et al. Estrogen and insulin-like growth factor-I (IGF-I) independently down-regulate critical repressors of breast cancer growth. Breast Cancer Res Treat 2012; 132: 61-73.

(8) Piva R, Pellegrino E, Mattioli M, Agnelli L, Lombardi L, Boccalatte F, et al. Functional validation of the anaplastic lymphoma kinase signature identifies CEBPB and BCL2A1 as critical target genes. J Clin Invest 2006; 116:3171-82.

(9) Sakamoto H, Tsukaguchi T, Hiroshima S, Kodama T, Kobayashi T, Fukami T A, et al. CH5424802, a selective ALK inhibitor capable of blocking the resistant gatekeeper mutant. Cancer Cell 2011; 19:679-90.

(10) Augustine C K, Jung S H, Sohn I, Yoo J S, Yoshimoto Y, Olson J A, Jr., et al. Gene expression signatures as a guide to treatment strategies for in-transit metastatic melanoma. Mol Cancer Ther 2010; 9:779-90.

(11) Augustine C K, Yoo J S, Potti A, Yoshimoto Y, Zipfel P A, Friedman H S, et al. Genomic and molecular profiling predicts response to temozolomide in melanoma. Clin Cancer Res 2009; 15:502-10.

(12) Raskin L, Fullen D R, Giordano T J, Thomas D G, Frohm M L, Cha K B, et al. Transcriptome Profiling Identifies HMGA2 as a Biomarker of Melanoma Progression and Prognosis. J Invest Dermatol 2013; 10.

(13) Bloethner S, Chen B, Hemminki K, Muller-Berghaus J, Ugurel S, Schadendorf D, et al. Effect of common B-RAF and N-RAS mutations on global gene expression in melanoma cell lines. Carcinogenesis 2005; 26:1224-32.

(14) Widmer D S, Cheng P F, Eichhoff O M, Belloni B C, Zipser M C, Schlegel N C, et al. Systematic classification of melanoma cells by phenotype-specific gene expression mapping. Pigment Cell Melanoma Res 2012; 25:343-53.

(15) Johnson W E, Li C, Rabinovic A. Adjusting batch effects in microarray expression data using empirical Bayes methods. Biostatistics 2007; 8:118-27.

(16) Hoek K S, Schlegel N C, Brafford P, Sucker A, Ugurel S, Kumar R, et al. Metastatic potential of melanomas defined by specific gene expression profiles with no BRAF signature. Pigment Cell Res 2006; 19:290-302.

(17) Chang C, Lin. LIBSVM: a library for support vector machines. ACM Transactions on Intelligent Systems and Technology 2011; 2:1-27.

(18) Johansson P, Pavey S, Hayward N. Confirmation of a BRAF mutation-associated gene expression signature in melanoma. Pigment Cell Res 2007; 20:216-21.

(19) Barretina J, Caponigro G, Stransky N, Venkatesan K, Margolin A A, Kim S, et al. The Cancer Cell Line Encyclopedia enables predictive modelling of anticancer drug sensitivity. Nature 2012; 483:603-7.

(20) Guyon I, Weston J, Barnhill S, Vapnik V. Gene Selection for Cancer Classification using Support Vector Machines. Machine Learning 2002; 46:389-422.

(21) Dry J R, Pavey S, Pratilas C A, Harbron C, Runswick S, Hodgson D, et al. Transcriptional pathway signatures predict MEK addiction and response to selumetinib (AZD6244). Cancer Res 2010; 70:2264-73.

(22) Assassi S, Mayes M D, Arnett F C, Gourh P, Agarwal S K, McNearney T A, et al. Systemic sclerosis and lupus: points in an interferon-mediated continuum. Arthritis Rheum 2010; 62:589-98.

(23) van M H, Gevaert O, Libbrecht L, Daemen A, Allemeersch J, Nevens F, et al. A seven-gene set associated with chronic hypoxia of prognostic importance in hepatocellular carcinoma. Clin Cancer Res 2010; 16:4278-88.

(24) Liu D, Hou P, Liu Z, Wu G, Xing M. Genetic alterations in the phosphoinositide 3-kinase/Akt signaling pathway confer sensitivity of thyroid cancer cells to therapeutic targeting of Akt and mammalian target of rapamycin. Cancer Res 2009; 69:7311-9.

(25) Liu D, Liu X, Xing M. Epigenetic genes regulated by the BRAFV600E signaling are associated with alterations in the methylation and expression of tumor suppressor genes and patient survival in melanoma. Biochem Biophys Res Commun 2012; 425:45-50.

We claim:

1. A method for treating BRAF-associated melanoma cancer in a patient sensitive to BRAF/MEK inhibitor treatment comprising the steps of:

(a) testing a sample of BRAF-mutated melanoma cells isolated from the patient and measuring expression levels of genes expressed in the following signaling pathways: TNFα, EGFR, IFNα, hypoxia, IFNγ, STAT3 and Myc;

(b) using a support vector machine algorithm to identify the patient as sensitive to BRAF/MEK inhibitor treatment based on the expression levels measured in step (a) and comparison to a reference; and (c) treating the patient identified as sensitive to BRAF/MEK inhibitor treatment with a BRAF/MEK inhibitor.

2. The method of claim 1, wherein the BRAF/MEK inhibitor comprises dabrafenib, sorafenib, vemurafenib, LGX818, GDC-0879, PLX-4720, trametinib, selumetinib, binimetinib, cobimetinib, refametinib CI1040, PD0325901 or combinations thereof.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: IFI6 forward primer

<400> SEQUENCE: 1
ggtctgcgat cctgaatggg              20

```
<210> SEQ ID NO 2
<211> LENGTH: 23
<212> TYPE: DNA
<213> ORGANISM: Artificial Sequence
<220> FEATURE:
<223> OTHER INFORMATION: IFI6 reverse primer

<400> SEQUENCE: 2
tcactatcga gatacttgtg ggt                                           23

<210> SEQ ID NO 3
<211> LENGTH: 20
<212> TYPE: DNA
<213> ORGANISM: Artificial Sequence
<220> FEATURE:
<223> OTHER INFORMATION: IFIT3 forward primer

<400> SEQUENCE: 3
agaacaaatc agcctggtca                                               20

<210> SEQ ID NO 4
<211> LENGTH: 20
<212> TYPE: DNA
<213> ORGANISM: Artificial Sequence
<220> FEATURE:
<223> OTHER INFORMATION: IFIT3 reverse primer

<400> SEQUENCE: 4
ccttgagaca ctgtcttcct                                               20

<210> SEQ ID NO 5
<211> LENGTH: 20
<212> TYPE: DNA
<213> ORGANISM: Artificial Sequence
<220> FEATURE:
<223> OTHER INFORMATION: STAT1 forward primer

<400> SEQUENCE: 5
ctgctccttt ggttgaatcc                                               20

<210> SEQ ID NO 6
<211> LENGTH: 22
<212> TYPE: DNA
<213> ORGANISM: Artificial Sequence
<220> FEATURE:
<223> OTHER INFORMATION: STAT1 reverse primer

<400> SEQUENCE: 6
gctgaagttc gtaccactga ga                                            22

<210> SEQ ID NO 7
<211> LENGTH: 23
<212> TYPE: DNA
<213> ORGANISM: Artificial Sequence
<220> FEATURE:
<223> OTHER INFORMATION: CCNG2 forward primer

<400> SEQUENCE: 7
tctgtattag ccttgtgcct tct                                           23

<210> SEQ ID NO 8
<211> LENGTH: 22
<212> TYPE: DNA
<213> ORGANISM: Artificial Sequence
<220> FEATURE:
<223> OTHER INFORMATION: CCNG2 reverse primer
```

<400> SEQUENCE: 8
ccttgaaacg atccaaacca ac                                               22

<210> SEQ ID NO 9
<211> LENGTH: 19
<212> TYPE: DNA
<213> ORGANISM: Artificial Sequence
<220> FEATURE:
<223> OTHER INFORMATION: WDR45L forward primer

<400> SEQUENCE: 9
ctcctgccgt gtaaccctc                                                   19

<210> SEQ ID NO 10
<211> LENGTH: 23
<212> TYPE: DNA
<213> ORGANISM: Artificial Sequence
<220> FEATURE:
<223> OTHER INFORMATION: WDR45L reverse primer

<400> SEQUENCE: 10
cccagatcat tactttgttg gga                                              23

<210> SEQ ID NO 11
<211> LENGTH: 21
<212> TYPE: DNA
<213> ORGANISM: Artificial Sequence
<220> FEATURE:
<223> OTHER INFORMATION: ERO1L forward primer

<400> SEQUENCE: 11
gccaggttag tggttacttg g                                                21

<210> SEQ ID NO 12
<211> LENGTH: 22
<212> TYPE: DNA
<213> ORGANISM: Artificial Sequence
<220> FEATURE:
<223> OTHER INFORMATION: ERO1L reverse primer

<400> SEQUENCE: 12
ggcctcttca ggtttacctt gt                                               22

<210> SEQ ID NO 13
<211> LENGTH: 22
<212> TYPE: DNA
<213> ORGANISM: Artificial Sequence
<220> FEATURE:
<223> OTHER INFORMATION: EGLN3 forward primer

<400> SEQUENCE: 13
ctgggcaaat actacgtcaa gg                                               22

<210> SEQ ID NO 14
<211> LENGTH: 19
<212> TYPE: DNA
<213> ORGANISM: Artificial Sequence
<220> FEATURE:
<223> OTHER INFORMATION: EGLN3 reverse primer

<400> SEQUENCE: 14
gaccatcacc gttggggtt                                                   19

<210> SEQ ID NO 15

```
<211> LENGTH: 22
<212> TYPE: DNA
<213> ORGANISM: Artificial Sequence
<220> FEATURE:
<223> OTHER INFORMATION: MAT1A forward primer

<400> SEQUENCE: 15
tcatgttcac atcggagtct gt                                              22

<210> SEQ ID NO 16
<211> LENGTH: 19
<212> TYPE: DNA
<213> ORGANISM: Artificial Sequence
<220> FEATURE:
<223> OTHER INFORMATION: MAT1A reverse primer

<400> SEQUENCE: 16
catgccggtc ttgcacact                                                  19

<210> SEQ ID NO 17
<211> LENGTH: 20
<212> TYPE: DNA
<213> ORGANISM: Artificial Sequence
<220> FEATURE:
<223> OTHER INFORMATION: RCL1 forward primer

<400> SEQUENCE: 17
aaggcaacag cactcccttt                                                 20

<210> SEQ ID NO 18
<211> LENGTH: 21
<212> TYPE: DNA
<213> ORGANISM: Artificial Sequence
<220> FEATURE:
<223> OTHER INFORMATION: RCL1 reverse primer

<400> SEQUENCE: 18
cccgtcgcac aatcttcagt t                                               21

<210> SEQ ID NO 19
<211> LENGTH: 21
<212> TYPE: DNA
<213> ORGANISM: Artificial Sequence
<220> FEATURE:
<223> OTHER INFORMATION: FGF21 forward primer

<400> SEQUENCE: 19
gccttgaagc cgggagttat t                                               21

<210> SEQ ID NO 20
<211> LENGTH: 20
<212> TYPE: DNA
<213> ORGANISM: Artificial Sequence
<220> FEATURE:
<223> OTHER INFORMATION: FGF21 reverse primer

<400> SEQUENCE: 20
gtggagcgat ccatacaggg                                                 20
```